(12) United States Patent
Bayly et al.

(10) Patent No.: US 7,405,229 B2
(45) Date of Patent: Jul. 29, 2008

(54) CATHEPSIN CYSTEINE PROTEASE INHIBITORS

(75) Inventors: Christopher Bayly, Beaconsfield (CA); Cameron Black, Baie d'Urfe (CA); Sheldon Crane, Pierrefonds (CA); Daniel J. McKay, Ottawa (CA); Renata Oballa, Kirkland (CA); Joel Robichaud, Dollard des Ormeaux (CA)

(73) Assignee: Merck Frosst Canada & Co., Quebec (CA)

( * ) Notice: Subject to any disclaimer, the term of this patent is extended or adjusted under 35 U.S.C. 154(b) by 0 days.

(21) Appl. No.: 10/560,672

(22) PCT Filed: Jun. 28, 2004

(86) PCT No.: PCT/CA2004/000948

§ 371 (c)(1), (2), (4) Date: Dec. 14, 2005

(87) PCT Pub. No.: WO2005/000800

PCT Pub. Date: Jan. 6, 2005

(65) Prior Publication Data

US 2007/0167635 A1     Jul. 19, 2007

Related U.S. Application Data

(60) Provisional application No. 60/483,678, filed on Jun. 30, 2003.

(51) Int. Cl.
*A61K 31/44* (2006.01)
*A61K 31/445* (2006.01)
*A61K 31/417* (2006.01)
*A61K 31/4184* (2006.01)
*C07D 211/80* (2006.01)
*C07D 233/54* (2006.01)
*C07D 235/04* (2006.01)

(52) U.S. Cl. ................ 514/329; 514/398; 546/192; 546/330; 548/335.1

(58) Field of Classification Search ............ 514/329, 514/398; 546/192, 330; 548/335.1
See application file for complete search history.

(56) References Cited

U.S. PATENT DOCUMENTS 6,313,117 B1 * 11/2001 Bekkali et al. ........... 514/235.5

FOREIGN PATENT DOCUMENTS

| WO | WO 01/96285 | 12/2001 |
| WO | WO 02/069901 | 9/2002 |
| WO | WO 03/041649 | 5/2003 |

OTHER PUBLICATIONS

Obach R.S., Drug-drug interactions; An important negative attribute in Drugs. Drugs of Today, 39(5), 301-38, 2003.*

* cited by examiner

*Primary Examiner*—Kamal Saeed
*Assistant Examiner*—Janet L Coppins
(74) *Attorney, Agent, or Firm*—Nicole M. Beeler; David A. Muthard

(57) ABSTRACT

This invention relates to a class of compounds having the general formula (I) which are cysteine protease inhibitors, including but not limited to, inhibitors of cathepsins K, L, S and B. These compounds are useful for treating diseases in which inhibition of bone resorption is indicated, such as osteoporosis.

7 Claims, No Drawings

CATHEPSIN CYSTEINE PROTEASE INHIBITORS

PRIORITY CLAIM

This application is a §371 National Stage Application of PCT/CA04/000948, filed on Jun. 28, 2004, which claims priority from U.S. Provisional Application Ser. No. 60/483,678, filed on Jun. 30, 2003.

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Osteoporosis is characterized by progressive loss of bone architecture and mineralization leading to the loss in bone strength and an increased fracture rate. The skeleton is constantly being remodeled by a balance between osteoblasts that lay down new bone and osteoclasts that breakdown, or resorb, bone. In some disease conditions and advancing age the balance between bone formation and resorption is disrupted; bone is removed at a faster rate. Such a prolonged imbalance of resorption over formation leads to weaker bone structure and a higher risk of fractures.

Bone resorption is primarily performed by osteoclasts, which are multinuclear giant cells. Osteoclasts resorb bone by forming an initial cellular attachment to bone tissue, followed by the formation of an extracellular compartment or lacunae. The lacunae are maintained at a low pH by a proton-ATP pump. The acidified environment in the lacunae allows for initial demineralization of bone followed by the degradation of bone proteins or collagen by proteases such as cysteine proteases. See Delaisse, J. M. et al., 1980, *Biochem J* 192: 365-368; Delaisse, J. et al., 1984, *Biochem Biophtys Res Commun*:441-447; Delaisse, J. M. et al., 1987, Bone 8:305-313, which are hereby incorporated by reference in their entirety. Collagen constitutes 95% of the organic matrix of bone. Therefore, proteases involved in collagen degradation are an essential component of bone turnover, and as a consequence, the development and progression of osteoporosis.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, C, F, H, L, K, O, S, V, W, and Z have been cloned. Cathepsin K (which is also known by the abbreviation cat K) is also known as cathepsin O and cathepsin $O_2$. See PCT Application WO 96/13523, Khepri Pharmaceuticals, Inc., published May 9, 1996, which is hereby incorporated by reference in its entirety. Cathepsin L is implicated in normal lysosomal proteolysis as well as several diseases states, including, but not limited to, metastasis of melanomas. Cathepsin S is implicated in Alzheimer's disease, atherosclerosis, chronic obstructive pulmonary disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. Increased Cathepsin B levels and redistribution of the enzyme are found in tumors, suggesting a role in tumor invasion and metastasis. In addition, aberrant Cathepsin B activity is implicated in such disease states as rheumatoid arthritis, osteoarthritis, pneumocystisis carinii, acute pancreatitis, inflammatory airway disease and bone and joint disorders.

Mammalian cathepsins are related to the papain-like cysteine proteases expressed by disease-causing parasites including those from the families protozoa, platyhelminthes, nematodes and arthropodes. These cysteine proteases play an essential role in the life cycle of these organisms.

Cysteine protease inhibitors such as E-64 (trans-epoxysuccinyl-L-leucylamide-(4-guanidino) butane) are known to be effective in inhibiting bone resorption. See Delaisse, J. M. et al., 1987, *Bone* 8:305-313, which is hereby incorporated by reference in its entirety. Recently, cathepsin K was cloned and found specifically expressed in osteoclasts See Tezuka, K. et al., 1994, *J. Biol Chem* 269:1106-1109; Shi, G. P. et al., 1995, *FEBS Lett* 357:129-134; Bromme, D. and Okamoto, K., 1995, *Biol Chem Hoppe Seyler* 376:379-384; Bromme, D. et al., 1996, *J Biol Chem* 271:2126-2132; Drake, F. H et al., 1996, *J Biol Chem* 271:12511-12516, which are hereby incorporated by reference in their entirety. Concurrent to the cloning, the autosomal recessive disorder, pycnodysostosis, characterized by an osteopetrotic phenotype with a decrease in bone resorption, was mapped to mutations present in the cathepsin K gene. To date, all mutations identified in the cathepsin K gene are known to eliminate collagenase activity. See Gelb, B. D. et al., 1996, *Science* 273:1236-1238; Johnson, M. R. et al., 1996, *Genome Res* 6:1050-1055; Hou, W.-S. et al., 1999 *J. Clin. Invest.* 103, 731-738 which are hereby incorporated by reference in their entirety. Therefore, it appears that cathepsin K is involved in osteoclast mediated bone resorption.

Cathepsin K is synthesized as a 37 kDa pre-pro enzyme, which is localized to the lysosomal compartment and where it is presumably autoactivated to the mature 27 kDa enzyme at low pH. See McQueney, M. S. et al., 1997, *J Biol Chem* 272:13955-13960; Littlewood-Evans, A. et al., 1997, *Bone* 20:81-86, which are hereby incorporated by reference in their entirety. Cathepsin K is most closely related to cathepsin S having 56% sequence identity at the amino acid level. The $S_2P_2$ substrate specificity of cathepsin K is similar to that of cathepsin S with a preference in the P1 and P2 positions for a positively charged residue such as arginine, and a hydrophobic residue such as phenylalanine or leucine, respectively. See Bromine, D. et al., 1996, *J Biol Chem* 271: 2126-2132; Bossard, M. J. et al., 1996, *J Biol Chem* 271:12517-12524,

3 which are hereby incorporated by reference in their entirety. Cathepsin K is active at a broad pH range with significant activity between pH 4-8, thus allowing for good catalytic activity in the resorption lacunae of osteoclasts where the pH is about 4-5.

Hurman type I collagen, the major collagen in bone is a good substrate for cathepsin K. See Kafienah, W., et al., 1998, *Biochem J* 331:727-732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T., et al., 1997, *J Biol Chem* 272:8109-8112, which is hereby incorporated by reference in its entirety. The crystal structure of cathepsin K has been resolved. See McGrath, M. E., et al., 1997, *Nat Struct Biol* 4:105-109; Zhao, B., et al., 1997, *Nat Struct Biol* 4: 109-11, which are hereby incorporated by reference in their entirety. Also, selective peptide based inhibitors of cathepsin K have been developed See Bromme, D., et al., 1996, *Biochem J* 315:85-89; Thomnpson, S. K., et al., 1997, *Proc Natl Acad Sci U S A* 94:14249-14254, which are hereby incorporated by reference in their entirety. Accordingly, inhibitors of Cathepsin K can reduce bone resorption. Such inhibitors would be useful in treating disorders involving bone resorption, such as osteoporosis.

SUMMARY OF THE INVENTION

The present invention relates to compounds that are capable of treating and/or preventing cathepsin dependent conditions or disease states in a mammal in need thereof. One embodiment of the present invention is illustrated by a compound of Formula L and the pharmaceutically acceptable salts, stereoisomers and N-oxide derivatives thereof:

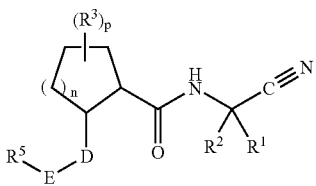

I

DETAILED DESCRIPTION OF THE INVENTION

The present invention relates to compounds of the following chemical formula:

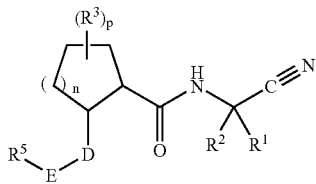

wherein
$R^1$ is hydrogen, $C_{1-6}$ alkyl or $C_{2-6}$ alkenyl wherein said alkyl and alkenyl groups are optionally substituted with $C_{3-6}$ cycloalkyl, —$SR^6$, —$SR^7$, —$SOR^6$, —$SOR^7$, —$SO_2R^6$, —$SO_2R^7$, —$SO_2CH(R^7)(R^9)$, —$OR^7$, —$OR^6$, —$N(R^7)_2$, one to six halo, aryl, heteroaryl or heterocycyl wherein said

4 aryl, heteroaryl and heterocycyl groups are optionally substituted with one or two substituents independently selected from the group consisting of $C_{1-6}$ alkyl, halo, hydroxyalkyl, hydroxy, alkoxy and keto;

$R^2$ is hydrogen, $C_{1-6}$ alkyl or $C_{2-6}$ alkenyl wherein said alkyl and alkenyl groups are optionally substituted with $C_{3-6}$ cycloalkyl, —$SR^6$, —$SR^7$, —$SOR^6$, —$SOR^7$, —$SO_2R^6$, —$SO_2R^7$, —$SO_2CH(R^7)(R^9)$, —$OR^7$, —$OR^6$, —$N(R^7)_2$, one to six halo, aryl, heteroaryl or heterocycyl wherein said aryl, heteroaryl and heterocycyl groups are optionally substituted with one or two substituents independently selected from the group consisting of $C_{1-6}$ alkyl, halo, hydroxyalkyl, hydroxy, alkoxy or keto; or $R^1$ and $R^2$ can be taken together with the carbon atom to which they are attached to form a $C_{3-8}$ cycloalkyl or heterocycyl ring wherein said ring system is optionally substituted with one or two substituents independently selected from the group consisting of $C_{1-6}$ alkyl, hydroxyalkyl, haloalkyl and halo;

each $R^3$ is independently selected from the group consisting of hydrogen, halo and $C_{1-2}$ alkyl wherein said alkyl group is optionally substituted with halo; or two $R^3$ groups can be taken together with the carbon atom to which they are attached to form a $C_{3-4}$ cycloalkyl ring, wherein said group is optionally substituted with halo;

D is $C_{1-3}$ alkyl, $C_{2-3}$ alkenyl, $C_{2-3}$ alkynyl, aryl, heteroaryl, $C_{3-8}$ cycloalkyl or heterocycyl wherein each said aryl, heteroaryl, cycloalkyl and heterocycyl groups, which may be monocyclic or bicyclic, is optionally substituted on either the carbon or the heteroatom with one to five substituents independently selected from the group consisting of $C_{1-6}$ alkyl, haloalkyl, halo, keto, alkoxy, —$SR^6$, —$SR^7$, —$OR^6$, —$OR^7$, $N(R^7)_2$, —$SO_2R^6$ and —$SO_2R^8$;

E is $C_{2-3}$ alkenyl, $C_{2-3}$ alkynyl, aryl, heteroaryl, $C_{3-8}$ cycloalkyl or heterocycyl wherein each said aryl, heteroaryl, cycloalkyl and heterocycyl groups, which may be monocyclic or bicyclic, is optionally substituted on either the carbon or the heteroatom with one to five substituents independently selected from the group consisting of $C_{1-6}$ alkyl, haloalkyl, halo, keto, alkoxy, —$SR^6$, —$SR^7$, —$OR^6$, —$OR^7$, $N(R^7)_2$, —$SO_2R^6$ and —$SO_2R^8$;

$R^5$ is hydrogen, $C_{1-6}$ alkyl, $C_{2-6}$ alkenyl, $C_{2-6}$ ailynyl, $C_{1-6}$ alkyloxy, halo, nitro, cyano, aryl, heteroaryl, $C_{3-8}$ cycloalkyl, heterocyclyl, —$C(O)OR^8$, —$C(O)OSi[CH(CH_3)_2]_3$, —$OR^6$, —$OR^8$, —$C(O)R^8$, —$R^8C(O)R^6$, —(O)$R^6$, —$C(O)N(R^a)(R^b)$, —$C(O)N(R^7)(R^7)$, —$C(O)N(R^8)(R^9)$, —$C(R^8)(R^9)OH$, —$SO_mR^7$, —$SO_mR^6$, —$R^8SR^6$, —$R^6$, —$C(R^6)_3$, —$C(R^8)(R^9)N(R^6)_2$, —$NR^8C(O)NR^8S(O)_2R^6$, —$SO_mN(R^c)(R^d)$, —$SO_mCH(R^8)(R^9)$, —$SO_m(C_{1-6}alkyl)C(O)(C_{0-6}alkyl)NR^{10}$, —$SO_m(C_{1-6}alkyl)N(R^{10})_2$, —$SO_m(C_{1-6}alkyl)R^{10}$; —$SO_m(C_{3-8}cycloalkyl)R^{10}$; —$SO_2N(R^8)C(O)(R^7)$, —$SO_2(R^8)C(O)N(R^7)_2$, —$OSO_2R^8$, —$N(R^8)(R^9)$, —$N(R^8)C(O)N(R^8)(R^6)$, —$N(R^8)C(O)R^6$, —$N(R^8)C(O)R^8$, —$N(R^8)C(O)OR^8$, —$N(R^8)S_2(R^8)$, —$C(R^8)(R^9)NR^8C(R^8)(R^9)R^6$, —$C(R^8)(R^9)N(R^8)R^6$, —$C(R^8)(R^9)N(R^8)(R^9)$, —$C(R^8)(R^9)SC(R^8)(R^9)(R^6)$, $R^8S$—, —$C(R^a)(R^b)Nr^aC(R^a)(R^b)(R^6)$, —$C(R^a)(R^b)N(R^a)(R^b)$, —$C(R^a)(R^b)C(R^a)(R^b)N(R^a)(R^b)$, —$C(O)C(R^a)(R^b)N(R^a)(R^b)$, —$C(R^a)(R^b)N(R^a)C(O)R^6$, —$C(O)C(R^a)(R^b)S(R^a)$, $C(R^a)(R^b)C(O)N(R^a)(R^b)$, —$B(OH)_2$, —$OCH_2O$— or 4,4,5,5-tetramethyl-1,3,2-dioxaborolan-2-yl; wherein said groups are optionally substituted on either the carbon or the heteroatom with one to five substituents independently selected from the group consisting of $C_{1-6}$ alkyl, halo, keto, cyano, haloalkyl, hydroxyalkyl, —$OR^6$, —$OR^7$, —$NO_2$, —$NH_2$, —$NHS(O)_2R^8$, —$R^6SO_2R^7$, —$SO_2R^7$, —$SO(R^7)$, —$SR^7$, —$SR^6$, —SO$_m$N(R$^c$)(R$^d$), —SO$_m$N(R$^8$)C(O)(R$^7$), —C(R$^8$)(R$^9$)N(R$^8$)(R$^9$), —C(R$^8$)(R$^9$)OH, —COOH, —C(O)(O)(R$^7$), —C(O)(O)C(R$^7$)$_3$, —C(R$^a$)(R$^b$)C(O)N(R$^a$)(R$^b$), —C(O)(R$^a$), —NH(R$^8$)C(R$^8$)(R$^9$)(R$^6$), —N(R$^8$)CO(R$^6$), —NH(CH$_2$)$_2$OH, —NHC(O)OR$^8$, —Si(CH$_3$)$_3$, heterocyclyl, aryl, heteroaryl, (C$_{1-4}$alkyl)heteroaryl and (C$_{1-4}$alkyl)aryl;

R$^6$ is hydrogen, aryl, aryl(C$_{1-4}$)alkyl, (C$_{1-4}$alkyl)aryl, heteroaryl, heteroaryl(C$_{1-4}$)alkyl, (C$_{1-4}$alkyl)heteroaryl, C$_{3-8}$ cycloalkyl, C$_{3-8}$ cycloalkyl(C$_{1-4}$)alkyl, or heterocyclyl (C$_{1-4}$)alkyl wherein said groups can be optionally substituted with one, two, or three substituents independently selected from the group consisting of halo, alkoxy and —SO$_2$R$^7$;

R$^7$ is hydrogen or C$_{1-6}$ alkyl which is optionally substituted with one, two, or three substituents independently selected from the group consisting of halo, alkoxy, cyano, —N(R$^8$)(R$^9$) and —SR$^8$;

R$^8$ is hydrogen or C$_{1-6}$ alkyl

R$^9$ is hydrogen or C$_{1-6}$ alkyl;

R$^{10}$ is hydrogen, C$_{1-6}$ alkyl, cyano, aryl, heteroaryl, heterocyclyl, SO$_m$heteroaryl, (C=N)O(C$_{1-6}$alkyl) or (C$_{1-6}$alkyl)NH(SO$_m$)heteroaryl;

R$^a$ is hydrogen, C$_{1-6}$ alkyl, (C$_{1-6}$ alklyl)aryl, (C$_{1-6}$ alkyl)hydroxyl, —O(C$_{1-6}$ alkyl), hydroxyl, halo, aryl, heteroaryl, C$_{3-8}$ cycloalkyl or heterocyclyl, wherein said alkyl, aryl, heteroaryl, C$_{3-8}$ cycloalkyl and heterocycyl can be optionally substituted on either the carbon or the heteroatopm with one, two, or three substituents independently selected from C$_{1-6}$ alkyl or halo;

R$^b$ is hydrogen, C$_{1-6}$ alkyl, (C$_{1-6}$ alkyl)aryl, (C$_{1-6}$ alkyl)hydroxyl, alkoxyl, hydroxyl, halo, aryl, heteroaryl, C$_{3-8}$ cycloalkyl or heterocycyl, wherein said alkyl, aryl heteroaryl, C$_{3-8}$ cycloalkyl and heterocycyl can be optionally substituted on either the carbon or the heteroatom with one, two, or three substituents independently selected from group consisting of C$_{1-6}$ alkyl and halo; or R$^a$ and R$^b$ can be taken together with the carbon atom to which they are attached or are between them to form a C$_{3-8}$ cycloalkyl ring or C$_{3-8}$ heterocycyl ring wherein said 3-8 membered ring system may be optionally substituted with one or two substituents independently selected from C$_{1-6}$ alkyl and halo;

R$^c$ is hydrogen or C$_{1-6}$ alkyl which is optionally substituted with one, two, or three substituents independently selected from the group consisting of halo and —OR$^6$;

R$^d$ is hydrogen or C$_{1-6}$ alkyl which is optionally substituted with one, two, or three substituents independently selected from the group consisting of halo and —OR$^6$; or R$^c$ and R$^d$ can be taken together with the nitrogen atom to which they are attached or are between them to form a C$_{3-8}$ heterocycyl ring which is optionally substituted with one or two substituents independently selected from the group consisting of C$_{1-6}$ alkyl, halo hydroxyalkyl, hydroxy, alkoxy and keto;

n is an integer from one to three;

m is an integer from zero to two;

p is an integer from one to three;

and the pharmaceutically acceptable salts, stereoisomers and N-oxide derivatives thereof.

In an embodiment of the invention, R$^1$ and R$^2$ are each hydrogen. In another embodiment of the invention, R$^1$ and R$^2$, when on the same carbon atom, can be taken together with the carbon atom to which they are attached to form a 3-8 membered cycloaLkyl ring system wherein said ring system is optionally substituted with C$_{1-6}$ alkyl, hydroxyalkyl, haloalkyl and halo. Examples of ring systems that can be formed include cyclopropyl, cyclobutyl, cyclopentyl, cyclohexyl and cycloheptyl. A preferred embodiment is when cyclopropyl is formed.

In another embodiment of the invention, R$^1$ and R$^2$ together with the carbon atom to which they are attached to form a 3-8 membered heterocyclyl ring system wherein said ring system is optionally substituted with C$_{1-6}$ alkyl, hydroxyalkyl, haloalkyl or halo. Examples of ring systems that can be formed include piperidinyl, pyrrolidinyl, or tetrahydropyranyl.

In an embodiment of the invention, each R$^3$ is hydrogen or halo. In a class of the embodiment, two R$^3$ groups are attached to the same carbon (geminal substitution). In subclass, each R$^3$ is halo. In a further subclass, each R$^3$ is fluoro.

In an embodiment of the invention, D is aryl or heteroaryl. Examples of preferred heteroaryl groups are pyridine, thiazole, isothiazole, oxazole, isoxazole, triazole, imidazole and thiadiazole. In an embodiment of the invention E is aryl or heteroaryl.

In an embodiment of the invention, R$^5$ is —SO$_m$R$^7$, —SO$_m$R$^6$, —R$^8$SR$^6$, SO$_m$N(R$^c$)(R$^d$), —SO$_m$CH(R$^8$)(R$^9$), —SO$_m$(C$_{1-6}$alkyl)C(O)(C$_{0-6}$alkyl)NR$^{10}$, —SO$_m$(C$_{1-6}$alkyl)N(R$^{10}$)$_2$, —SO$_m$(C$_{1-6}$alky)R$^{10}$; —SO$_m$(C$_{3-8}$cycloalkyl)R$^{10}$; —SO$_2$N(R$^8$)C(O)(R$^7$) or —SO$_2$(R$^8$)C(O)N(R$^7$)$_2$; wherein said groups are optionally substituted on either the carbon or the heteroatom with one to five substituents independently selected from the group consisting of C$_{1-6}$ alkyl, halo, keto, cyano, haloalkyl, hydroxyalkyl, —OR$^6$, —OR$^7$, —NO$_2$, —NH$_2$, —NHS(O)$_2$R$^8$, —R$^6$SO$_2$R$^7$, —SO$_2$R$^7$, —SO(R$^7$), —SR$^7$, —SR$^6$, —SO$_m$N(R$^c$)(R$^d$), —SO$_m$N(R$^8$)C(O)(R$^7$), —C(R$^8$)(R$^9$)N(R$^8$)(R$^9$), —C(R$^8$)(R$^9$)OH, —COOH, —C(O)(O)(R$^7$), —C(O)(O)C(R$^7$)$_3$, —C(R$^a$)(R$^b$)C(O)N(R$^a$)(R$^b$), —C(O)(R$^a$), —N(R$^8$)C(R$^8$)(R$^9$)(R$^6$), —N(R$^8$)CO(R$^6$), —NH(CH$_2$)$_2$OH, —NHC(O)OR$^8$, —Si(CH$_3$)$_3$, heterocyclyl, aryl, heteroaryl, (C$_{1-4}$alkyl)heteroaryl and (C$_{1-4}$alkyl)aryl.

In an embodiment of the invention, n is two.

In an embodiment of the invention, p is one. In another embodiment of the invention, p is two. In another embodiment of the invention, p is three.

In an embodiment of the invention, R$^a$ and R$^b$ are defined such that they can be taken together with the carbon or nitrogen to which they are attached to form a monocyclic or bicyclic carbocycle or heterocycle with 5-7 members in each ring. The heterocycle can optionally contain, in addition to the nitrogen, 1 or 2 additional heteroatoms selected from N, O and S. Said carbocycle and heterocycle can be optionally substituted with one or more substituents selected from C$_{1-6}$ alkyl and halo.

Reference to the preferred embodiments set forth above is meant to include all combinations of particular and preferred groups unless stated otherwise.

Specific embodiments of the present invention include, but are not limited to:

2-(2-bromophenyl)-N-cyanomethyl-5,5-difluorocyclohexanecarboxamide;

2-(2-bromophenyl)-N-cyanomethyl-5,5-difluorocyclohexanecarboxamide;

N-(cyanomethyl)-5,5-difluoro-2-[4'-(methylthio)-1,1'-biphenyl-2-yl]cyclohexanecarboxamide;

N-(cyanomethyl)-5,5-difluoro-2-[4'-(methylthio)-1,1'-biphenyl-2-yl]cyclohexanecarboxamide;

N-(cyanomethyl)-5,5-difluoro-2-[4'-(methylthio)-1,1'-biphenyl-2-yl]cyclohexanecarboxamide;

N-(1-(cyanocyclopropyl)-5,5-difluoro-2-[4'-(methylthio)-1,1'-biphenyl-2-yl]cyclohexanecarboxamide;

N-(1-(cyanocyclopropyl)-5,5-difluoro-2-[4'-(methylthio)-1,1'-biphenyl-2-yl]cyclohexanecarboxamide;
N-(1-cyanocyclopropyl)-5,5-difluoro-2-[4'-(methylthio)-1,1'-biphenyl-2-yl]cyclohexanecarboxamide;
2-[4'-(benzyloxy)-1,1'-biphenyl-2-yl]-N-(cyanomethyl)cyclohexanecarboxamide;
N-(cyanomethyl)-2-(4'-hydroxy-1,1'-biphenyl-2-yl)cyclohexanecarboxamide;
N-(cyanomethyl)-2-(4'-fluoro-1,1'-biphenyl-2-yl)cyclohexanecarboxamide;
N-(cyanomethyl)-2-[4'-(methylsulfonyl)-1,1'-biphenyl-2-yl]cyclohexanecarboxamide;
N-(cyanomethyl)-5,5-difluoro-2-4'-fluoro-1,1'-biphenyl-2-yl)cyclohexanecarboxamide;
N-(cyanomethyl)-2-(4'-vinyl-1,1'-biphenyl-2-yl)cyclohexanecarboxamide;
N-(cyanomethyl)-2-(4'-cyclopropyl-1,1'-biphenyl-2-yl)cyclohexanecarboxamide;
N-(cyanomethyl)-5,5-difluoro-2-[5-(methylsulfonyl)-4'-(methylthio)-1,1'-biphenyl-2-yl]cyclohexanecarboxamide;
N-(1-(cyanocyclopropyl)-5,5-difluoro-2-[5-(methylsulfonyl)-4'-(methylthio)-1,1'-biphenyl-2-yl]cyclohexanecarboxamide;
N-(cyanomethyl)-2-{4'-[(fluoromethyl)thio]-1,1'-biphenyl-2-yl}cyclohexanecarboxamide;
N-(cyanomethyl)-2-(2'-methyl-1,1'-biphenyl-2-yl)cyclohexanecarboxmide;
N-(cyanomethyl)-2-(4'-methyl-1,1'-biphenyl-2-yl)cyclohexanecarboxamide;
N-(cyanomethyl)-2-(4'-ethyl-1,1'-biphenyl-2-yl)cyclohexanecarboxamide;
N-(cyanomethyl)-2-(4'-propyl-1,1'-biphenyl-2-yl)cyclohexanecarboxamide;
N-(cyanomethyl)-2-(3'-isopropyl-1,1'-biphenyl-2-yl)cyclohexanecarboxamide;
N-(cyanomethyl)-2-(4'-isopropyl-1,1'-biphenyl-2-yl)cyclohexanecarboxamide;
2-(4'-tert-butyl-1,1'-biphenyl-2-yl)-N-(cyanomethyl)cyclohexanecarboxamide;
N-(cyanomethyl)-2-[3'-(trifluoromethyl)-1,1'-biphenyl-2-yl]cyclohexanecarboxamide;
N-(cyanomethyl)-2-(3'-fluoro-1,1'-biphenyl-2-yl)cyclohexanecarboxamide;
N-(cyanomethyl)-2-(2'-fluoro-1,1'-biphenyl-2-yl)cyclohexanecarboxamide;
2-(4'-(chloro-1,1'-biphenyl-2-yl)-N-(cyanomethyl)cyclohexanecarboxamide;
2-(3'-chloro-1,1'-biphenyl-2-yl)-N-(cyanomethyl)cyclohexanecarboxamide;
N-(cyanomethyl)-2-[3'-hydroxymethyl)-1,1'-biphenyl-2-yl]cyclohexanecarboxamide;
2'-(2-{[(cyanomethyl)amino]carbonyl}cyclohexyl)-1,1'-biphenyl-3-carboxylic acid;
2'-(2-{[(cyanomethyl)amino]carbonyl}cyclohexyl)-1,1'-biphenyl-4-carboxylic acid;
N-(cyanomethyl)-2-(3'-methoxy-1,1'-biphenyl-2-yl)cyclohexanecarboxamide;
N-(cyanomethyl)-2-(2'-ethoxy-1,1'-biphenyl-2-yl)cyclohexanecarboxamide;
N-(cyanomethyl)-2-(4'-ethoxy-1,1'-biphenyl-2-yl)cyclohexanecarboxamide;
N-(cyanomethyl)-2-(3'-isopropoxy-1,1'-biphenyl-2-yl)cyclohexanecarboxamide;
N-(cyanomethyl)-2-(4'-isopropoxy-1,1'-biphenyl-2-yl)cyclohexanecarboxamide;
N-(cyanomethyl)-2-(4'-phenoxy-1,1-biphenyl-2-yl)cyclohexanecarboxamide;
N-(cyanomethyl)-2-[4'-(trifluoromethoxy)-1,1'-biphenyl-2-yl]cyclohexanecarboxamide;
N-(cyanomethyl)-2-[2'-(methylthio)-1,1'-biphenyl-2-yl]cyclohexanecarboxamide;
N-(cyanomethyl)-2-[3'-(methylthio)-1,1'-biphenyl-2-yl]cyclohexanecarboxamide;
N-(cyanomethyl)-2-[4'-ethylthio)-1,1'-biphenyl-2-yl]cyclohexanecarboxamide;
2-(3'-amino-1,1'-biphenyl-2-yl)-N-(cyanomethyl)cyclohexanecarboxamide;
N-(cyanomethyl)-2-[4'-dimethylamino)-1,1'-biphenyl-2-yl]cyclohexanecarboxamide;
N-(cyanomethyl)-2-(3'-nitro-1,1'-biphenyl-2-yl)cyclohexanecarboxamide;
2-[3'-(acetylamino)-1,1'-biphenyl-2-yl]-N-(cyanomethyl)cyclohexanecarboxamide;
N-(cyanomethyl)-2-(4'-isobutyl-1,1'-biphenyl-2-yl)cyclohexanecarboxamide;
N-(cyanomethyl)-2-(2-pyridin-4-ylphenyl)cyclohexanecarboxamide;
N-(cyanomethyl)-2-(2-quinolin-8-ylphenyl)cyclohexanecarboxamide;
N-(cyanomethyl)-2-[2-(2-methoxypyrimidin-5-yl)phenyl]cyclohexanecarboxamide;
N-(cyanomethyl)-2-(2-pyridin-3-ylphenyl)cyclohexanecarboxamide;
N-(cyanomethyl)-2-(2-thien-3-ylphenyl)cyclohexanecarboxamide;
2-(4'-acetyl-1,1'-biphenyl-2-yl)-N-(cyanomethyl)cyclohexanecarboxamide;
N-(cyanomethyl)-2-(1,1':2',1''-terphenyl-2-yl)cyclohexanecarboxamide;
2-(4'-cyano-1,1'-biphenyl-2-yl)-N-(cyanomethyl)cyclohexanecarboxamide;
2-(3'-cyano-1,1'-biphenyl-2-yl)-N-(cyanomethyl)cyclohexanecarboxamide;
6-(3-bromophenyl)-N-(cyanomethyl)cyclohex-3-ene-1-carboxamide;
2-(3-bromophenyl)-N-(cyanomethyl)cyclohexanecarboxamide;
tert-butyl 4-[3'-(2-{[(cyanomethyl)amino]carbonyl}cyclobexyl)-1,1'-biphenyl-4-yl]piperazine-1-carboxylate;
N-(cyanomethyl)-2-(4'-piperazin-1-yl-1,1'-biphenyl-3-yl)cyclohexanecarboxamide;
2-(3-bromophenyl)-N-(cyanomethyl)-4-methylcyclopentanecarboxamide;
(4R)-2-(3-bromophenyl)-N-(cyanomethyl)-4-methylcyclopentanecarboxamide;
N-(cyanomethyl)-2-(4-methoxy-1,1'-biphenyl-3-yl)cyclohexanecarboxamide;
N-(cyanomethyl)-2-[4'-(methylthio)-1,1'-biphenyl-3-yl]cyclohexanecarboxamide;
N-(cyanomethyl)-2-[4'-(methylsulfonyl)-1,1'-biphenyl-3-yl]cyclohexanecarboxamide;
N-(cyanomethyl)-2-(5-phenyl-1,3-oxazol-2-yl)cyclohexanecarboxamide;
N-(cyanomethyl)-2-(5-phenyl-1,3-thiazol-2-yl)cyclohexanecarboxamide;
N-(cyanomethyl)-2-(5-phenyl-1,3-thiazol-2-yl)cyclohexanecarboxamide;
2-(2-bromophenyl)-N-(cyanomethyl)cyclohexanecarboxamide;
N-(cyanomethyl)-2-[4'-(methylthio)-1,1'-biphenyl-2-yl]cyclohexanecarboxamide;

N-(cyanomethyl)-2-phenylcyclohexanecarboxamide;
5,5-dichloro-N-(cyanomethyl)-2-[4'-(methylthio)-1,1'-biphenyl-2-yl]cyclohexanecarboxamide;
N-(cyanomethyl)-5,5-difluoro-2-{1-methyl-3-[4-mnethylthio)phenyl]-1H-pyrazol-4-yl}cyclohexanecarboxanide;
6-(2-bromophenyl)-N-(cyanomethyl)spiro[2.5]octane-5-carboxamide;
2-(3-bromo-1-methyl-1H-pyrazol-4-yl-N-(cyanomethyl)-5,5-difluorocyclohexanecarboxamide;
N-(cyanomethyl)-6-[4'-(methylthio)-1,1'-biphenyt-2-yl]spiro[2.5]octane-5-carboxamide;
2-(2-bromophenyl)-5,5-dichloro-N-(cyanomethyl)cyclohexanecarboxamide;
2-(3-bromo-1-methyl-1H-pyrazol-4-yl)-5,5-dichloro-N-(cyanomethyl)cyclohexanecarboxamide;
N-(cyanomethyl)-2-{(Z)-2-[4-(methylthio)phenyl]ethenyl}cyclohexanecarboxamide;
N-(cyanomethyl)-2-{2-[4-(methylthio)phenyl]ethyl}cyclohexanecarboxamide;
N-(cyanomethyl)-2-{(Z)-2-[4-(methylsulfonyl)phenyl]ethenyl}cyclohexanecarboxamide;
N-(cyanomethyl)-2-{2-[4-(methylsulfonyl)phenyl]ethyl}cyclohexanecarboxamide;
N-(cyanomethyl)-2-((Z)-2-{4-[(trifluoromethyl)thio]phenyl}ethenyl)cyclohexanecarboxamide;
N-(cyanomethyl)-2-{(E)-2-[4-(methylsulfonyl)phenyl]ethenyl}cyclohexanecarboxamide;
N-(cyanomethyl)-2-(2-{4-[(trifluoromethyl)thio]phenyl}ethyl)cyclohexanecarboxamide;
N-(cyanomethyl)-2-ethynylcyclohexanecarboxamide;
N-(cyanomethyl)-2-{[4-(methylthio)phenyl]ethynyl}cyclohexanecarboxamide;
N-(cyanomethyl)-2-{[4-(methylsulfonyl)phenyl]ethynyl}cyclohexanecarboxamide;
N-(cyanomethyl)-2-({4-[(trifluoromethyl)thio]phenyl}ethynyl)cyclohexanecarboxamide;
N-(cyanomethyl)-2-phenylethynyl)cyclohexanecarboxamide;
2-[(4-bromophenyl)ethynyl]-N-(cyanomethyl)cyclohexanecarboxamide;
2(1,1'-biphenyl-4-ylethynyl)-N-(cyanomethyl)cyclohexanecarboxamide;
N-(cyanomethyl)-2-{[4'-(methylthio)-1,1'-biphenyl-4-yl]ethynyl}cyclohexanecarboxamide;
N-(cyanomethyl)-2-[(3-fluorophenyl)ethynyl]cyclohexanecarboxamide;
2-[(3-chlorophenyl)ethynyl]-N-(cyanomethyl)cyclohexanecarboxamide;
N-(cyanomethyl)-2-[(4-pyridin-4-ylphenyl)ethynyl]cyclohexanecarboxamide;
2-[(3-bromophenyl)ethynyl]-N-(cyanomethyl)cyclohexanecarboxamide;
2-(1,1'-biphenyl-3-ylethynyl)-N-(cyanomethyl)cyclohexanecarboxamide;
2-[(2-bromophenyl)ethynyl]-N-(cyanomethyl)cyclohexanecarboxamide;
2-(1,1'-biphenyl-2-ylethynyl)-N-(cyanomethyl)cyclohexanecarboxamide;
N-(cyanomethyl)-2-{[4-(6-methoxypyridin-2-yl)thien-3-yl]ethynyl}yclohexanecarboxamide;
N-(cyanomethyl)-2-{4'-[(cyanomethyl)thio]biphenyl-2yl}-5,5-duorocyclohexanecarboxamide;
2-{4'-[(2-amino-2-oxoethyl)thio]biphenyl-2-yl}-N-(cyanomety)-5,5-diuorocyclohexanecarboxamide;

N-(cyanomethyl)-2-[4'-({2-[(cyanomethyl)amino]-2-oxoethyl}thio)biphenyl-2-yl]-5,5-difluorocyclohexanecarboxamide;
N-(cyanomethyl)-5,5-difluoro-2-{4'-[(2-pyridin-2-ylethyl)thio]biphenyl-2-yl}cyclohexanecarboxamide;
N-(cyanomethyl)-5,5-difluoro-2-{4'-[(pyridin-2-ylmethyl)thio]biphenyl-2-yl}cyclohexanecarboxamide;
N-(cyanomethyl)-5,5-difluoro-2-{4'-[(pyridin-3-ylmethyl)thio]biphenyl-2-yl}cyclohexanecarboxamide;
N-(cyanomethyl)-5,5-difluoro-2-{4'-[(pyridin-4-ylmethyl)thio]biphenyl-2-yl}cyclohexanecarboxamide;
2-{4'-[(1H-benzimidazol-2-ylmethyl)thio]biphenyl-2-yl}-N-(cyanomethyl)-5,5-difluorocyclohexanecarboxamide;
2-{4'-[(1H-benzimidazol-6-ylmethyl)thio]biphenyl-2-yl}-N-(cyanomethyl)-5,5-difluorocyclohexanecarboxamide;
N-(cyanomethyl)-5,5-difluoro-2-{4'-[(1H-imidazol-4-ylmethyl)thio]biphenyl-2-yl}cyclohexanecarboxamide;
N-(cyanomethyl)-5,5-difluoro-2-{4'-[(1H-imidazol-2-ylmethyl)thio]biphenyl-2-yl}cyclohexanecarboxamide;
N-(cyanomethyl)-5,5-difluoro-2-[4'-({[1-(1H-imidazol-2-ylmethyl)-1H-imidazol-2-yl]methylthio}biphenyl-2-yl]cyclohexanecarboxamide;
N-(cyanomethyl)-5,5-difluoro-2-(4'-{[2-(1H-imidazol-4-yl)ethyl]thiol}biphenyl-2-yl)cyclohexanecarboxamide;
N-(cyanomethyl)-5,5-difluoro-2-4'-{[2-(1H-imidazol-2-yl)ethyl]thio}biphenyl-2-yl)cyclohexanecarboxamide;
N-(cyanomethyl)-5,5-difluoro-2-(4'-{[(1-methylpiperidin-4-yl)methyl]thio}biphenyl-2-yl)cyclohexanecarboxamide;
N-(cyanomethyl)-5,5-difluor-2-(4'-{[2-(1-methylpiperidin-4-yl)ethyl]thio}biphenyl-2-yl)cyclohexanecarboxamide;
N-(cyanomethyl)-5,5-difluoro-2-[2'-fluoro-4'-(methylthio)biphenyl-2-yl]cyclohexanecarboxade;
N-(cyanomethyl)-5,5-difluoro-2-(4'-{[(5-phenyl-1H-imidazol-2-yl)methyl]thio}biphenyl-2-yl)cyclohexanecarboxamide;
N-(cyanomethyl)-5,5-difluoro-2-{4'-[(2-pyridin-4-ylethyl)thio]biphenyl-2-yl}cyclohexanecarboxamide;
N-(cyanomethyl)-5,5-difluoro-2-[4'-({2-[(pyridin-2-ylsulfonyl)amino]ethyl}thio)biphenyl-2-yl]cyclohexanecarboxarnide;
N-(cyanomethyl)-5,5-difluoro-2-(4'-{[2-((pyridin-2-ylsulfonyl){2-[(pyridin-2-ylsulfonyl)amino]ethyl}amino)ethyl]thio}biphenyl-2-yl)cyclohexanecarboxamide;
N-(cyanomethyl)-5,5-difluoro-2-{4'-[(1H-tetrazol-5-ylmethyl)thio]biphenyl-2-yl}cyclohexanecarboxamide;
2-{4'-[(1-cyanocyclopropyl)thio]biphenyl-2-yl}-N-(cyanomethyl)-5,5-difluorocyclohexanecarboxamide;
methyl 1-{[2'-(2-{[(cyanomethyl)amino]carbonyl}-4,4-difluorocyclohexyl)biphenyl-4-yl]thio}cyclopropanecarboximidoate;
2-(4'-{[2-(1H-benzimidazol-2-yl)ethyl]thio}biphenyl-2-yl)-N-(cyanomethyl)-5,5-difluorocyclohexanecarboxamide;
2-{4'-[(1H-benzimidazol-7-ylmethyl)thiol]biphenyl-2-yl}-N-(cyanomethyl)-5,5-difluorocyclohexanecarboxamide;
N-(cyanomethyl)-5,5-difluoro-2-[4'-{2-[(methylsulfonyl)amino]ethyl}thio)biphenyl-2-yl]cyclohexanecarboxamide;
N-(cyanomethyl)-5,5-difluoro-2-(4'-{2-[(methylsulfonyl)amino]ethyl}biphenyl-2-yl)cyclohexanecarboxamide;

and the pharmaceutically acceptable salts, stereoisomers and N-oxide derivatives thereof.

Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The compounds of the present invention are inhibitors of cathepsins and are therefore useful to treat or prevent cathepsin dependent diseases or conditions in mammals, preferably humans. Specifically, the compounds of the present invention are inhibitors of Cathepsin K and are therefore useful to treat or prevent Cathepsin K dependent diseases or conditions in mammals, preferably humans.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, chronic obstructive pulnonary disease and cancer including metastatic bone disease, hypercalcemia of malignancy, and multiple rnyeloma. In treating such conditions with the instantly claimed compounds, the required therapeutic amount will vary according to the specific disease and is readily ascertainable by those skilled in the art Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the narnmal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a manual in need thereof, comprising administering to the mammal a therapeutically effective amount of any of the compounds or any of the pharmaceutical compositions described above. The utility of cathepsin K inhibitors in the inhibition of bone resorption is known in the literature, see Stroup, G. B., Lark, M. W., Veber, D F., Bhattacharrya, A., Blake, S., Dare, L. C., Erhard, Kay., Hoffian, S. J., James, L E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746; 2001; and Votta, B. J., Levy, M. A., Badger, A., Dodds, R. A., James, L E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention is a method of treating or preventing osteoporosis in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P., Hunziker, E., Wehmeyer, O., Jones, S., Boyde, A., Rommersldrch, W., Moritz, J. D., Schu, P., and Vonfigura, K. Impaired osteoclast bone resorption leads to osteopetrosis in cathepsin K-deficient mice. Proc. Natl. Acad. Sci. USA 95:13453-13458; 1998.

Another embodiment of the invention is a method of treating or preventing rheumatoid arthritic condition in a mammal in need thereof, comprising administering to the mammal a therapeutically effective amount of any of the compounds or any of the pharmaceutical compositions described above. It is known in the literature that progressive destruction of the periarticular bone is a major cause of joint dysfunction and disability in patients with rheumatoid arthritis (RA), see Goldring SR, "Pathogenesis of bone erosions in rheumatoid arthritis". Curr. Opin. Rheumatol. 2002; 14: 406-10. Analysis of joint tissues from patients with RA have provided evidence that cathepsin K positive osteoclasts are the cell types that mediate the focal bone resorption associated with rheumatoid synovial lesion, see Hour W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74. In addition, generalized bone loss is a major cause of morbidity associated with severe RA. The frequency of hip and spinal fractures is substantially increased in patients with chronic RA, see Gould A, Sambrook, P, Devlin J et al, "Osteoclastic activation is the principal mechanism leading to secondary osteoporosis in rheumatoid arthritis". J. Rheumatol. 1998; 25: 1282-9. The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions described above. It is known in the literature that osteoarthritis (OA) is accompanied with well-defined changes in the joints, including erosion of the articular cartilage surface, peri-articular endochondral ossification/osteophytosis, and subchondral bony sclerosis and cyst formation, see Oettneier R, Abendroth, K, "Osteoarthritis and bone: osteologic types of osteoarthritis of the hip", Skeletal Radiol. 1989; 18: 165-74. Recently, the potential contribution of subchondral bone sclerosis to the initiation and progression of OA have been suggested. Stiffened subchondaal bone as the joint responding to repetitive impulsive loading, is less able to attenuate and distribute forces through the joint, subjecting it to greater mechanical stress across the articular cartilage surface. This in turn accelerates cartilage wear and fibrillate, see Radin, E L and Rose R M, "Role of subchondral bone in the initiation and progression of cartilage damage", Clin. Orthop. 1986; 213: 34-40. Inhibition of excessive subarticular bone resorption by an anti-resorptive agent such as a cathepsin K inhibitor, will lead to inhibition of subchondral bone turnover, thus may have a favorable impact on OA progression.

In addition to the above hypothesis, cathepsin K protein expression was recently identified in synovial fibroblasts, macrophage-like cells, and chondrocytes from synovium and articular cartilage specimens derived from OA patients, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synoviun", Arthritis Rheumatism 2002; 46: 663-74; and Dodd, R A, Connor, J R, Drake, F H, Gowen, M, "Expression of Cathepsin K messenger RNA in giant cells and their precursors in human osteoarthritic synovial tissues". Arthritis Rheumatism 1999; 42: 1588-93; and Konttinen, Y T, Mandelin, J, Li, T-F, Salo, J, Lassus, J et al. "Acidic cysteine endoproteinase cathepsin K in the degeneration of the superficial articular hyaline cartilage in osteoarthritis", Arthritis Rheumatism 2002; 46: 953-60. These recent studies thus implicated the role of cathepsin K in the destruction of collagen type II in the articular cartilage associated with the progression of osteoarthritis. The utility of cathepsin K inhibitors in the treatment or prevention of osteoartritis as described in this invention thus comprise of two different mechanisms, one is on the inhibition of osteoclastriven subchondral bone turnover, and two is on the direct inhibition of collagen type II degeneration in the synovium and cartilage of patients with OA.

Another embodiment of the invention is a method of treating cancer in a mammel in need thereof, comprising administering to the mammal a therapeutically effective amount of any of the compounds or any of the pharmaceutical compositions described above. It is known in the literature that cathepsin K is expressed in human breast carcinoma, prostate cancer and chordoma and has matrix degrading capabilities, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma." Cancer Res 1997 Dec. 1; 57(23):5386-90,. Brubaker K D, Vessella R L, True L D, Thomas R, Corey E "Cathepsin K MRNA and protein expression in prostate cancer progression." J Bone Miner Res 2003 18, 222-30, Haeckel C, Krueger S, Kuester D, Ostertag H, Samii M, Buehling F, Broemme D, Czerniak B, Roessner A. "Expression of cathepsin K in chordoma." Hum Pathol 2000 July;31(7):83440.

Another embodiment of the invention is a method of treating atherosclerosis in a mammal in need thereof, comprising administering to the mammal a therapeutically effective amount of any of the compounds or any of the pharmaceutical compositions described above. It is known in the literature that cathepsin K is expressed in human atheroma and has significant elastase activity, see Sukhova G K, Shi G P, Simon D I, Chapman H A, Libby P. "Expression of the elastolytic cathepsins S and K in human atheroma and regulation of their production in smooth muscle cells." J Clin Invest 1998 August 102, 576-83.

Another embodiment of the invention is a method of treating obesity in a mammal in need thereof, comprising administering to the mammal a therapeutically effective amount of any of the compounds or any of the pharmaceutical compositions described above. It is known in the literature that cathepsin K mRNA is increased in adipose tissue in several mouse models of obesity and also in adipose tissue of obese human males, see Chiellini C, Costa M, Noveffi S E, Amri E Z, Benzi L, Bertacca A, Cohen P, Del Prato S, Friedman J M, Maffei M. "Identification of cathepsin K as a novel marker of adiposity in white adipose tissue." J Cell Physiol 2003, 195, 309-21.

Another embodiment of the invention is a method of treating chronic obstructive pulmonary disease in a mammal in need thereof, comprising administering to the mammal a therapeutically effective amount of any of the compounds or any of the pharmaceutical compositions described above. It is known in the literature that cathepsin K plays a role in lung fibrosis, see Buhling, F., et al., "Pivotal role of cathepsin K in lung fibrosis," Am J Pathol. 2004 June;164(6):2203-16.

Another embodiment of the invention is a method of treating parasitic infections in a mamma in need thereof, comprising administering to the mammal a therapeutically effective amount of any of the compounds or any of the pharmaceutical compositions described above. It is known in the literature that mammalian cathepsins are related to the papain-like cysteine proteases which play an important role in the life cycle of these parasites. Such parasites are involved in the diseases of malaria, American trypanosomiasis, African trypanosomiasis, leishmaniasis, giardiasis, trichomoniasis, amoebiasis, schistosomiasis, fasciohas is, paragonimiasis and intestinal roundworms, see Lecaille F, Kaleta J, Bromme D., Human and parasitic papain-like cysteine proteases: their role in physiology and pathology and recent developments in inhibitor design. Chem Rev 2002 102, 4459-88.

Another embodiment of the invention is a method of treating severe acute respiratory syndrome (SARS) in a mammal in need thereof, comprising administering to the mammal a therapeutically effective amount of any of the compounds or any of the pharmaceutical compositions described above.

Another embodiment of the invention is a method of treating metastatic bone disease in a mammal in need thereof, comprising administering to the mammal a therapeutically effective amount of any of the compounds or any of the pharmaceutical compositions described above. It is known in the literature that osteoclasts are responsible for bone resorption and that bone destruction and hypercalcemia induced by metastatic tumors are carried out by osteoclasts. Accordingly, the inhibition of osteoclasts can prevent bone destruction and bone metastasis, see Miyamoto, T. and Suda, T., "Differentiation and function of osteoclasts," Keio J Med 2003 March; 52(1):1-7.

Another embodiment of the invention is administering to a mammal a therapeutically effective amount of any of the compounds or any of the pharmaceutical compositions described above for the treatment of mammalian diseases associated with cathepsin S including Alzheimer's disease, atherosclerosis, chronic obstructive pulmonary disease, cancer and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. It is known in the literature that cathepsin S activity is associated with the above disease states, see Munger J S, Haass C, Lemere C A, Shi G P, Wong W S, Teplow D B, Selkoe D J, Chapman H A. Lysosomal processing of amyloid precursor protein to A beta peptides: a distinct role for cathepsin S. Biochem J 1995 311, 299-305, Sukhova G K, Zhang Y, Pan J H, Wada Y, Yarnamoto T, Naito M, Kodama T, Tsimikas S, Witztum J L, Lu M L, Sakara Y, Chin M T, Libby P, Shi G P. Deficiency of cathepsin S reduces atherosclerosis in LDL receptor-deficient mice. J Clin Invest 2003 111, 897-906, Zheng T, Zhu Z, Wang Z, Homner R J, Ma B, Riese R J Jr, Chapman H A Jr, Shapiro S D, Elias J A. Inducible targeting of IL-13 to the adult lung causes matrix metalloproteinase- and cathepsin-dependent emphysema. J Clin Invest 2000 106, 1081-93, Shi G P, Sukhova G K, Kuzuya M, Ye Q, Du J, Dbang Y, Pan J H, Lu M L, Cheng X W, Iguchi A, Perrey S, Lee A M, Chapman H A, Libby P. Deficiency of the cysteine protease cathepsin S impairs. microvessel growth. Circ Res 2003 92, 493-500, Nakagawa T Y, Brissette W H, Lira P D, Griffiths R J, Petrushova N, Stock J, McNeish J D, Eastman S E, Howard E D, Clarke S R, Rosloniec E F, Elliott E A, Rudensky A Y. Impaired invariant chain degradation and antigen presentation and diminished collagen-induced artritis in cathepsin S null mice. Immunity 1999 10,207-17.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn'starch For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, rnannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxyrnethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylarnine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic.acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds are also useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; an estrogen receptor modulator, an androgen receptor modulator; an inhibitor of osteoclast proton ATPase; an inhibitor of HMG-CoA reductase; an integrin receptor antagonist; an osteoblast anabolic agent, such as PTH; a Nonsteroidal anti-inflammatory drug; a selective cyclooxygenase-2 inhibitor, an inhibitor of interleukin-1 beta; a LOX/COX inhibitor, and the pharmaceutically acceptable salts and mixtures thereof. A preferred combination is a compound of the present invention and an organic bisphosphonate. Another preferred combination is a compound of the present invention and an estrogen receptor modulator. Another preferred combination is a compound of the present invention and an androgen receptor modulator. Another preferred combination is a compound of the present invention and an osteoblast anabolic agent "Organic bisphosphonate" includes, but is not limited to, compounds of the chemical formula

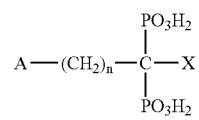

wherein n is an integer from 0 to 7 and wherein A and X are independently selected from the group consisting of H OH, halogen, $NH_2$, SH phenyl, $C_1$-$C_{30}$ alky, $C_3$-$C_{30}$ branched or cycloalkyl, bicyclic ring structure containing two or three N, $C_1$-$C_{30}$ substituted alkyl, $C_1$-$C_{10}$ alkyl substituted $NH_2$, $C_3$-$C_{10}$ branched-or cycloalkyl substituted $NH_2$, $C_1$-$C_{10}$ dialkyl substituted $NH_2$, $C_1$-$C_{10}$ alkoxy, $C_1$-$C_{10}$ alkyl substituted thio, thiophenyl, halophenylthio, $C_1$-$C_{10}$ alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a $C_3$-$C_{10}$ ring.

In the foregoing chemical formula, the aikyl groups can be straight, branched, or cyclic, provided sufficient atoms are selected for the chemical formula The $C_1$-$C_{30}$ substituted alkyl can include a wide variety of substituents, nonlimiting examples which include those selected from the group consisting of phenyl, pyridyl, furanyl, pyrrolidinyl, imidazonyl, $NH_2$, $C_1$-$C_{10}$ alkyl or dialkyl substituted $NH_2$, OH, SH, and $C_1$-$C_{10}$ alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra- $C_1$-$C_{10}$-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronate, which is also known as alendronic acid, 4-amino-1-hydroxybutylidene-1,1-bisphosphonic acid, alendronate sodium or alendronate monosodium trihydrate, 4-amino-1-hydroxybutylidene-1,1-bisphosphonic acid monosodium trihydrate.

Alendronate is described in U.S. Pat. No. 4,922,007, to Kieczykowsli et al., issued May 1, 1990; U.S. Pat. No. 5,019,651, to Kieczykowsli et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cirnadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (BB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 μg/kg body weight and preferably about 10 to about 2000 μg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-immethyl-2-[4-[2-(1-piperidinyl)ethoxy]phenyl]-2H-1-benzopyran-3-yl]-phenyl-2,2-dimethylpropanoate, 4,4'-diydroxybenzophenone-2,4-dimtrophenyl-hydrazone, and SH646.

An "estrogen receptor beta modulator" is a compound that selectively agonizes or antagonizes estrogen receptor beta (ER☐ Agonizing ER☐ increases transcription of the tryptophan hydroxylase gene (TPH, the key enzyme in serotonin synthesis) via an ER☐ mediated event. Examples of estrogen receptor beta agonists can be found in PCT International publication WO 01/82923, which published on Nov. 8, 2001, and WO 02/41835, which published on May 20, 2002, both of which are hereby incorporated by reference in their entirety.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the arL For example, see the assays described or cited in U.S. Pat. No. 4,231,938 at col. 6, and WO 84/02131 at pp. 30-33. The terms "MG-CoA reductase inhibitor" and "inhibitor of HMG-CoA reductase" have the same meaning when used herein.

Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885, 314. The term HMG-CoA reductase inhibitor as used herein includes all pharmaceutically acceptable lactone and open-acid forms (i.e., where the lactone ring is opened to form the free acid) as well as salt and ester forms of compounds which have HMG-COA reductase inhibitory activity, and therefor the use of such salts, esters, open-acid and lactone forms is included within the scope of this invention. An illustration of the lactone portion and its corresponding open-acid form is shown below as structures I and II.

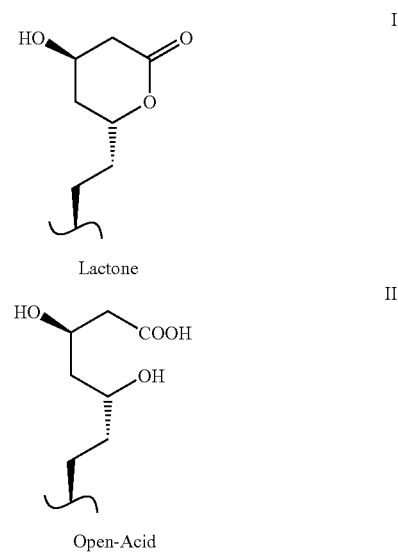

Lactone

Open-Acid

In HMG-CoA reductase inhibitors where an open-acid form can exist, salt and ester forms may preferably be formed from the open-acid, and all such forms are included within the m g of the term "BMG-oA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from arnines such as ammonia, ethylenediamine, N-methylglucamine, lysine, arginine, omnithine, choline, N,N'-dibenzylethylenediamine, chloroprocaine, diethanolamine, procaine, N-benzylphenethylamnine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, karate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, rnalate, maleate, mandelate, mesylate, rnethylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-COA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha_v\beta_5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the 4 $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of 4 $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ intergrins. H. N. Lode and coworkers in PNAS USA 96: 1591-1596 (1999) have observed synergistic effects between an antiangiogenic $\alpha_v$ integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The $\alpha$ and $\beta$ integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by RM Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: inplications for the pathogenesis of humoral hypercalcemia of malignancy," JCEM 86: 1525-1531 (2001)] and may also have potential as anabolic agents for treating osteoporosis.

"Nonsteroidal anti-inflammatory drugs" or NSAIDs, inhibit the metabolism of arachidonic acid to proinflammatory prostaglandins via cyclooxygenase (COX)-1 and COX-2. Nonlimiting examples of NSAIDs include: aspirin, ibuprofen, naproxen, diclofenac, etodolac, fenoporfen, flubiprofen, indomethacin, ketoprofen, ketorolac, meloxicam, nabumetone, oxaprozin, piroxican, sulindac, tolmetin, diflunisal, meclofenamate and phenylbutazone.

A "selective cyclooxygenase-2 inhibitor," or COX-2 inhibitor, refers to a type of nonsteroidal anti-inflammatory drug (NSAID). that inhibit the COX-2 coenzyme, which contributes to pain and inflammation in the body. Nonlimiting examples of COX-2 inhibitos include: celecoxib, etoricoxib, parecoxib, rofecoxib, valdecoxib and lumiracoxib.

An "inhibitor of interleukin-1 beta" or IL-1β refers to in inhibitors of IL-1 which is a soluble factor produced by monocytes, macrophages, and other cells which activates T-lymphocytes and potentiates their response to mitogens or antigens. Nonlimiting examples of IL-1B inhibitors include diacerein and rhein.

A "LOX/COX inhibitor" refers to an inhibitor or all three of the major enzymes involved in arachidonic acid pathway—namely, 5-LOX, COX-1 and COX-2. A nonimiting example of a LOX/COX inhibitor is licofelone.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: preventing the disease, i.e. causing the clinical symptoms of the disease not to develop in a mammal that may be exposed to or predisposed to the disease but does not yet experience or display symptoms of the disease; inhibiting the disease, i.e., arresting or reducing the development of the disease or its clinical symptoms; or relieving the disease, i.e., causing regression of the disease or its clinical symptoms.

The term "bone resorption," as used herein, refers to the process by which osteoclasts degrade bone.

The present invention also encompasses a pharmaceutical composition useful in the treatment of osteoporosis or other bone disorders, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kgtday, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of the instantly claimed compounds in combination with a second agent selected from: an organic bisphosphonate; an estrogen receptor modulator; an androgen receptor modulator; an inhibitor of osteoclast proton ATPase; an inhibitor of HMG-oA reductase; an integrin receptor antagonist; an osteoblast anabolic agent, such as PTH; a Nonsteroidal anti-inflammatory drug; a selective cyclooxygenase-2 inhibitor; an inhibitor of interleukin-1 beta; a LOX/COX inhibitor and the pharmaceutically acceptable salts and mixtures thereof.

These and other aspects of the invention will be apparent from the teachings contained herein.

Definitions

The compounds of the present invention may have asymmetric centers, chiral axes, and chiral planes (as described in: E. L. Bliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted. For example, any claim to compound A below is understood to include tautomeric structure B, and vice versa, as well as mixtures thereof.

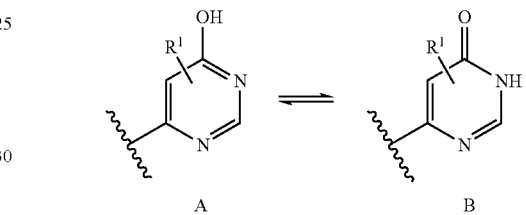

When any variable (e.g. $R^1$, $R^2$, $R^a$ etc.) occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring carbon atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be taken to be equivalent to the phrase "optionally substituted with at least one substituent" and in such cases the preferred embodiment will have from zero to three substituents.

As used herein, "alkyl" is intended to include both branched and straight-chain saturated aliphatic hydrocarbon groups having one to ten carbon atoms unless otherwise specified. For example, $C_1$-$C_{10}$, as in "$C_1$-$C_{10}$ alkyl" is defined to include groups having 1, 2, 3, 4, 5, 6, 7, 8, 9 or 10 carbons in a linear, branched, or cyclic arrangement. For example, "$C_1$-$C_{10}$ alkyl" specifically includes methyl, ethyl, propyl, butyl, pentyl, hexyl, heptyl, octyl, nonyl, decyl, and so on.

"Alkoxy" or "alkyloxy" represents an alkyl group as defined above, unless otherwise indicated, wherein said alkyl group is attached through an oxygen bridge. Examples of alkoxy include methoxy, ethoxy and the like.

The term "cycloalkyl" or "carbocycle" shall mean cyclic rings of alkanes of three to eight total carbon atoms, unless otherwise indicated, or any number within this range (i.e., cyclopropyl, cyclobutyl, cyclopentyl, cyclohexyl, cycloheptyl or cyclooctyl).

If no number of carbon atoms is specified, the term "alkenyl" refers to a non-aromatic hydrocarbon radical, straight or branched, containing from 2 to 10 carbon atoms and at least 1 carbon to carbon double bond. Preferably, 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight or branched, containing from 2 to 10 carbon atoms, unless otherwise specified, containing at least 1 carbon to carbon triple bond. Up to 3 carbon-carbon triple bonds may be present. Thus, "$C_2$-$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkyl group may contain triple bonds and may be substituted if a substituted alkynyl group is indicated.

In certain instances, substituents may be defined with a range of carbons that includes zero, such as ($C_0$-$C_6$)alkylene-aryl. If aryl is taken to be phenyl, this definition would include phenyl itself as well as —$CH_2$Ph, —$CH_2CH_2$Ph, $CH(CH_3)$ $CH_2CH(CH_3)$Ph, and so on.

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl. In cases where the aryl substituent is bicyclic and one ring is non-aromatic, it is understood that attachment is via the aromatic ring.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofinatanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzbimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromnatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

As appreciated by those of skill in the art, "halo" or "halogen" as used herein is intended to include chloro, fluoro, bromo and iodo. The term "keto" means carbonyl (C=O).

The term "haloalkyl" means an alkyl radical as defined above, unless otherwise specified, that is substituted with one to five, preferably one to three halogen. Representative examples include, but are not limited to trifluoromethyl, dichloroethyl, and the like.

The term "hydroxyalkyl" means a linear monovalent hydrocarbon radical of one to six carbon atoms or a branched monovalent hydrocarbon radical of three to six carbons substituted with one or two hydroxy groups, provided that if-two hydroxy groups are present they are not both on the same carbon atom. Representative examples include, but are not limited to, hydroxymethyl, 2-hydroxyethyl, 2-hydroxypropyl, 3-hydroxypropyl, and the like.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

The present invention also includes N-oxide derivatives and protected derivatives of compounds of Formula I. For example, when compounds of Formula I contain an oxidizable nitrogen atom, the nitrogen atom can be converted to an N-oxide by methods well known in the arL Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

Whenever the term "alkyl" or "aryl" or either of their prefix roots appear in a name of a substituent (e.g., aryl $C_{0-8}$ alkyl) it shall be interpreted as including those limitations given above for "alkyl" and "aryl." Designated numbers of carbon atoms (e.g., $C_{1-10}$) shall refer independently to the number of carbon atoms in an alkyl or cyclic alkyl moiety or to the alkyl portion of a larger substituent in which alkyl appears as its prefix root.

The pharmaceutically acceptable salts of the compounds of this invention include the conventional non-toxic salts of the compounds of this invention as formed inorganic or organic acids. For example, conventional non-toxic salts include those derived from inorganic acids such as hydrochloric, hydrobromic, sulfiric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, trifluoroacetic and the like. The preparation of the pharmaceutically acceptable salts described above and other typical pharmaceutically acceptable salts is more fully described by Berg et al., "Pharmaceutical Salts," *J. Pharm: Sci,* 1977:66:1-19, hereby incorporated by reference. The pharmaceutically acceptable salts of the compounds of this invention can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base.

For purposes of this specification, the following abbreviations have the indicated meanings:
BuLi=normal butyl lithium
CBr$_4$=tetrabromomethane
CH$_2$Cl$_2$=methylene chloride
CHCl$_3$=chloroform
(CH$_3$O)$_2$CO=dimethyl carbonate
DAST=diethylaminosulfuir trifluoride
DIBAL-H=diisobutylaluminum hydride
DIPEA=diisopropylethylamine
DMF=N,N-irnethylformamide
DMSO=dimethylsulfoxide
Et$_3$N=triethylamine
EtOH=ethanol
KH$_2$PO$_4$=potassium dihydrogenphosphate
HCl=hydrochloric acid
MeOH=methanol
MgBr=magnesium bromide
MgSO$_4$=magnesium sulfate
Na$_2$CO$_3$=sodium carbonate
NaOMe=sodium methoxide
Na$_2$SO$_4$=sodium sulfate
PCl$_5$=phosphorous pentachloride
PdCl$_2$(dppf)=[1,1'-bis(diphenylphosphino)ferrocene]dichloropalladium(II)
PG=protecting group
PPh$_3$=triphenylphosphine
Pr$_2$NEt=N,Ndiisopropylethylamine
PyBOP=benzotriazol-1-yloxytris(pyrrolidino)phosphonium-hexafluorophosphate
rt=room temperature
sat aq.=saturated aqueous
TBAF=tetrabutylammonium fluoride
TfO=trifluoromethanesulfonate
THF=tetrahydrofinan
tlc=thin layer chromatography
TMSBr=bromotrimethylsilane
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl The novel compounds of the present invention can be prepared according to the following general procedures using appropriate materials and are further exemplified by the following specific examples. The compounds illustrated in the examples are not, however, to be construed as forming the only genus that is considered as the invention. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted.

SCHEMES

Compounds of the present invention can be prepared according to Scheme 1, as indicated below. Thus, an unsaturated or saturated (obtained by hydrogenation of the olefin) cyclic carboxylic acid (see Sakito, Y.; Suzukamo, G. *Chem. Lett.* 1986, 621-624 (n=1) and Morin, R.; Manuel, C.; Mazmanian, C. *Eur. J. Med. Chem.* 1976, 11, 493-499 (n=2)) can be coupled to an appropriately substituted aminoacetonitrile to provide compounds of the current invention. If the substituent on D system is a halogen, a palladium-catalyzed Suzuki coupling with an appropriate boronic acid provides additional compounds of the current invention as shown.

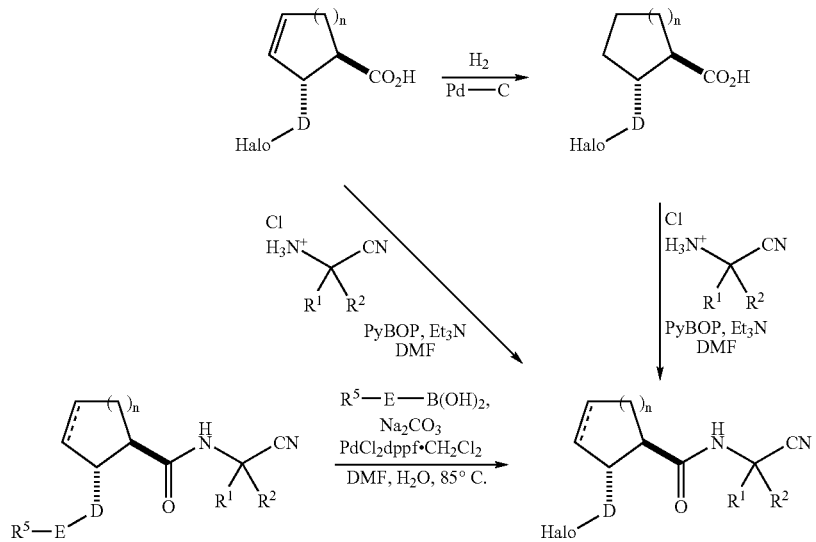

SCHEME 1

Compounds of the present invention may be prepared according to Scheme 2, as indicated below. Thus, the unsaturated acid from Scheme 1 can be converted to a bromolactone with TMSBr/DMSO/DIPEA (see Miyashita, K.; Tanaka, A.; Mizuno, H.; Tanaka, M.; Iwata, C. *J. Chem Soc. Perkin Trans.* 1,1994, 847-851). Methoxide catalyzed opening of the lactone affords a bromohydroxyester that is converted to the corresponding ketone by oxidation of the alcohol followed by reductive debrorination, with zinc for example. This ketone is subsequently converted to the corresponding gem-difluoro ($R^3,R^4$=F) or gem-dichloro ($R^3,R^4$=Cl) compounds by treatment with DAST or $PCl_5$ respectively. Alternatively, this ketone can be transformed into the corresponding exo-methylene compound by a Wittig reaction using a methyl triphenylphosphoniurn salt and further to spiro-cyclopropane derivatives via a Simraons-Smith type cyclopropanation reaction and still further to gem-dimethyl ($R^3$, $R^4$=$CH_3$) derivatives by treatment of the cyclopropane product with hydrogen in the presence of a suitable catalyst. Hydrolysis of the ester functionality with aqueous base, and peptide coupling and Suzuki reaction as described in Scheme 1 affords compounds of the current invention that possess a variety of substituents on the cycloalkyl fragment.

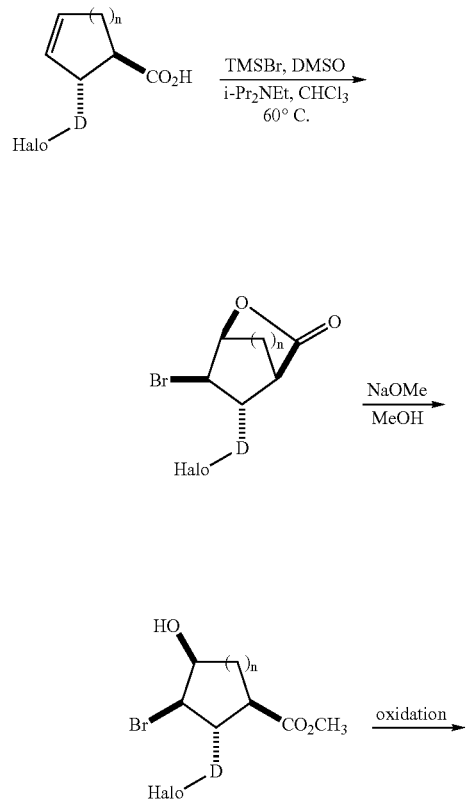

SCHEME 2

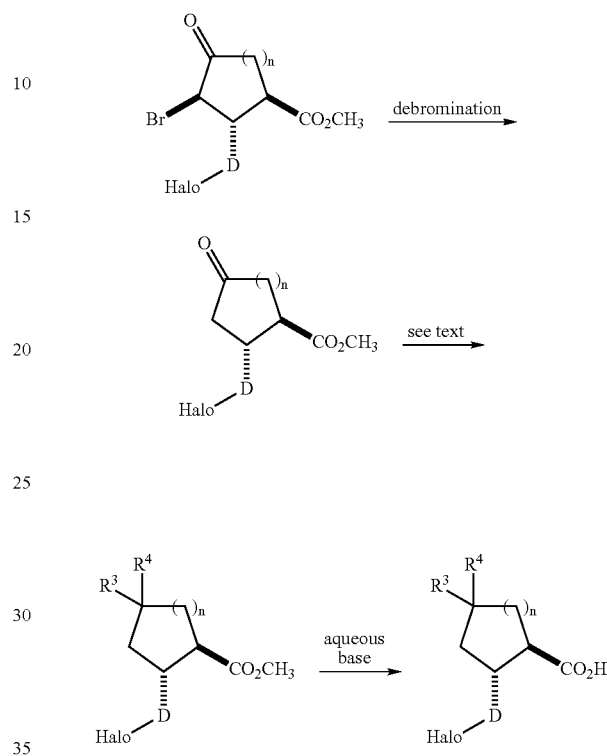

Compounds of the current invention may also be prepared according to Scheme 3. Thus, a suitably substituted cycloalkanone (such as $R^3,R^4$=F; Cl; spiro-cyclopropyl or CH3; see Patrick, T. B.; Scheibel, J. J.; Cantrell, G. L. *J. Org. Chem.* 1981, 46, 3917-3918; Harmata, M.; Shao, L. *Synthesis* 1999, 1534-1540; Crandall, J. K.; Seidewand, R. J. *J. Org. Chem.* 1970, 35, 697-701; or Negishi, E.; Chatterjee, S. *Tetrahedron Lett.* 1983, 24, 1341-1344, respectively) can be converted to the α,β unsaturated ketoester by treatment with a suitable base such as sodium hydride and subsequent quenching of the resulting enolate anion with dimethyl carbonate followed by oxidation with $PhSeCl/pyr/H_2O_2$. This compound can then serve as an electrophile in conjugate addition reactions with a variety of nucleophiles such as, but not limited to, bifunctional organocopper reagents. Reductive removal of the ketone functionality via the tosylhydrazone (see Taber, D. F; Malcolm, S. C. *J. Org. Chem.* 1998, 63, 3717-3721), or alternatively by Raney nickel desulfurization of the corresponding thioacetal (see Newman, M. S.; Walborsky, H. M. *J. Am. Chem. Soc.,* 1950, 72, 4296-4297), followed by ester hydrolysis and peptide coupling as described in Scheme 2 yields compounds of the current invention. When X is a protected oxygen functionality, a Suzuki reaction (via the triflate) followed by ester hydrolysis and peptide coupling as described in Scheme 2 provides compounds of the current invention.

SCHEME 3

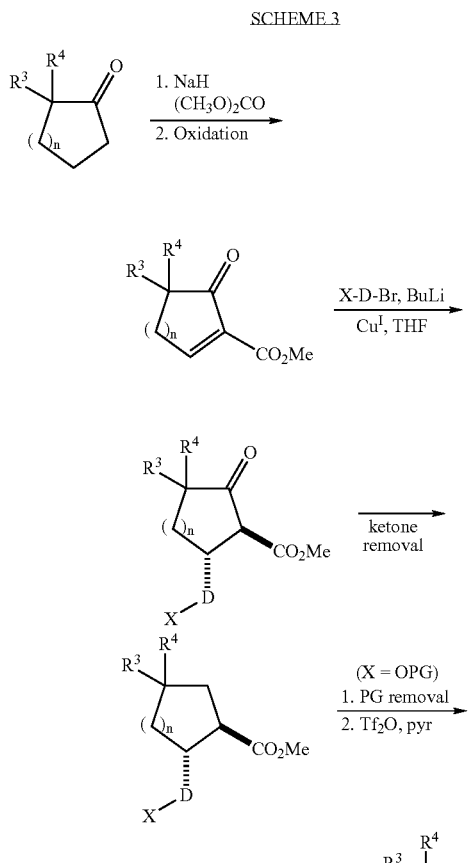

SCHEME 4

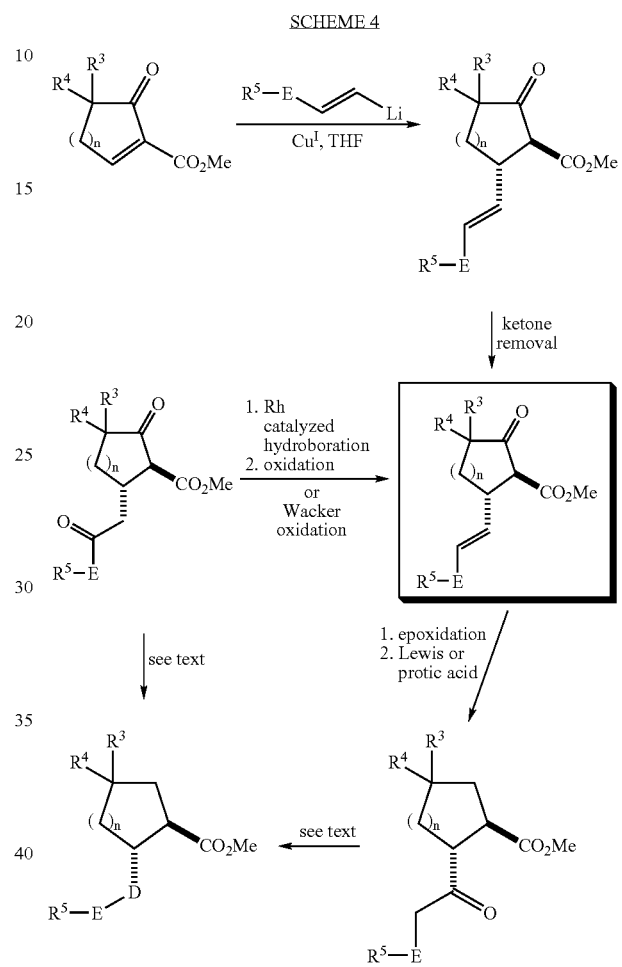

isoxazole, triazole, imidazole, thiadizaole, etc., according to well established literature precedents (see Gauthier, J. Y. et al. *Bioorg. Med. Chem. Lett.*1996, 6, 87-92 and references therein). Ester hydrolysis and peptide coupling as per Scheme 1 yields compounds of the current invention.

A diverse array of compounds of the current invention where D is a heterocycle can be prepared as shown in Scheme 4. Copper mediated conjugate addition of a vinyl lithium or magnesium species to the α,β unsaturated ketoester from Scheme 3 followed by ketone removal as discussed for scheme 2 affords a versatile intermediate olefin (boxed) that can be selectively converted (when E=aryl or heteroaryl) to one of two regioisomeric ketones by subjecting it to either a rhodium catalyzed hydroboration (see Hayashi, T.; Matsumoto, Y. *Tetrahedron. Asymmetry* 1991, 2, 601-612 and references therein), oxidation sequence or alternatively a Wacker oxidation in one case or epoxidation followed by an acid catalyzed epoxide rearrangement (see Ranu, B. C.; Jana, U. *J. Org. Chem,* 1998, 63, 8212-16 and references therein) in the other. These ketones may also be interconverted through a carbonyl transposition sequence via the corresponding α phenylsulfenylketones (see Trost, B. M.; Hiroi, K.; Kurozumi, S. *J. Am. Chem. Soc.,* 1975, 97, 438-440). Each of these α methylene-ketones can then be further transformed into a variety of heterocycles, such as thiazole, isothiazole, oxazole, Compounds of the current invention may also be prepared according to Scheme 5a. Addition of a vinyl (m=0) or allyl (m=1) Grignard reagent to the α,β unsaturated ketoester from Scheme 3 in the presence of a suitable copper (I) catalyst affords the conjugate addition product. Reductive removal of the ketone and reaction with ozone leads to the corresponding aldehyde. The aldehyde derived from the conjugate addition of vinyl Grignard (m=0) to the α,β unsaturated ketoester can be transformed into a terminal alkyne with $CBr_4$, $PPh_3$ and base. A Sonagashira reaction then gives another versatile intermediate (boxed) that can be utilized to prepare compounds of the current invention where D=alkene, alkyne or heterocycle as indicated. Alternatively, this intermediate can be accessed, as shown in Scheme 5b, through direct 1,4-addition of the alkyne fragment (see Eriksson, M.; Iliefski, T.; Nilsson, M.; Olsson, T. *J. Org. Chem.* 1997, 62, 182-187) to the previously mentioned α,β unsaturated ketoester from Scheme 3.

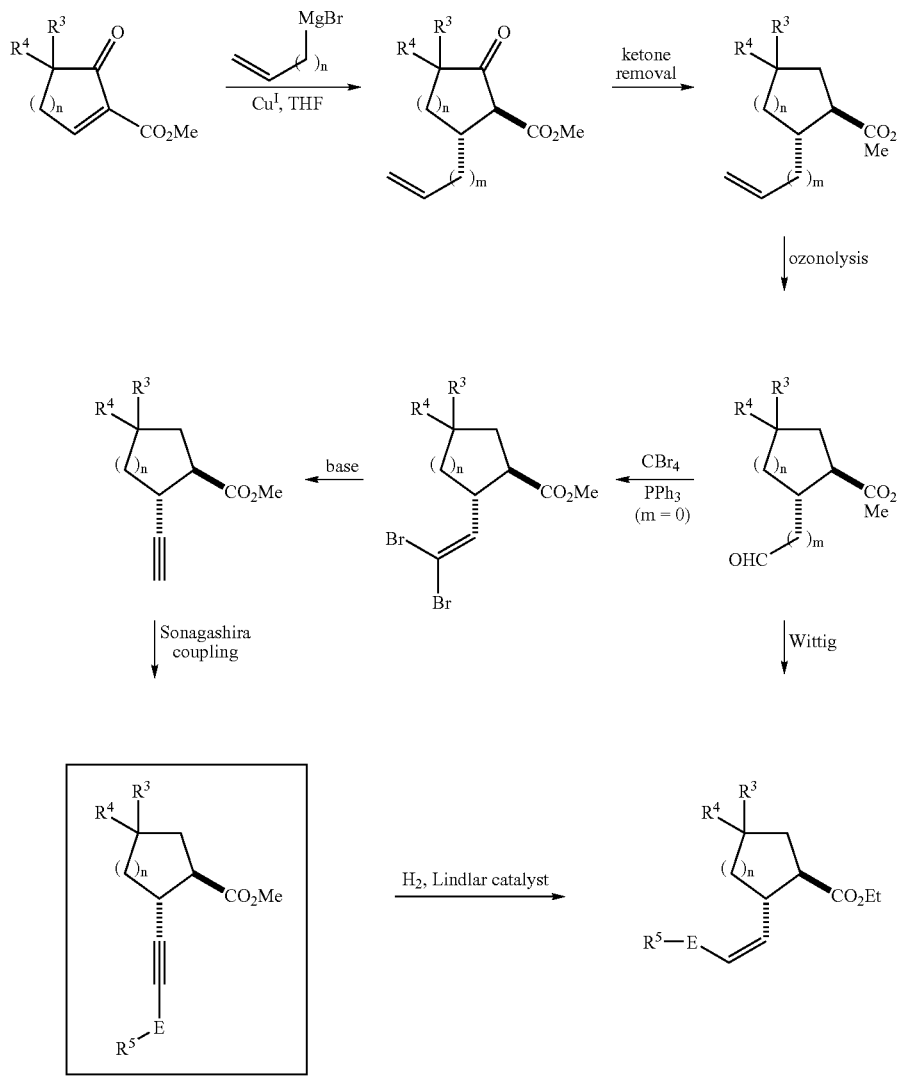
SCHEME 5A
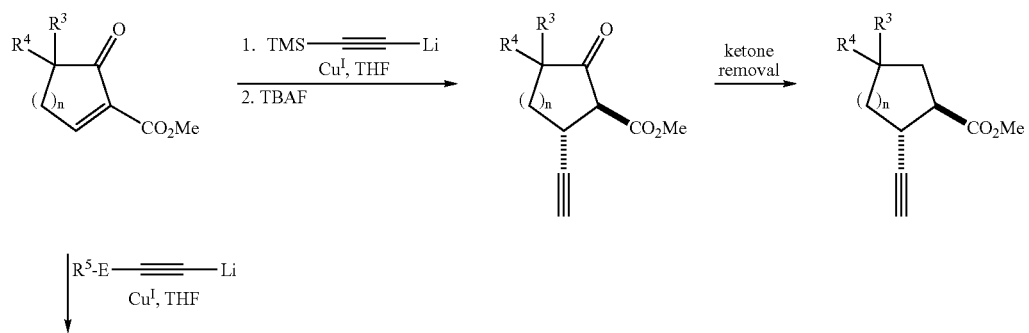
SCHEME 5B

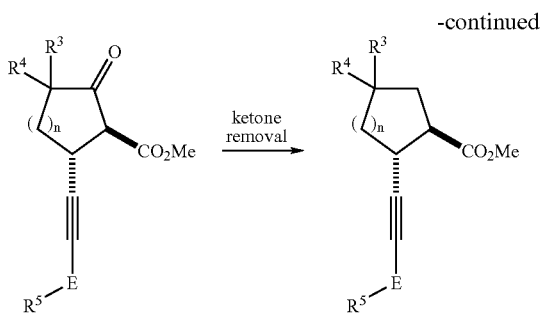

Compounds of the current invention may also be prepared according to the chemistry outlined in Scheme 5c. Thus, Grignard addition to the homologous aldehyde intermediates (m=0, m=1), that were generated by ozonolysis of the corresponding terminal olefins in Scheme 5a, followed by oxidation of the resulting alcohol affords the regioisomeric α methylene ketones and subsequently compounds of the current invention according to Scheme 4.

SCHEME 5C

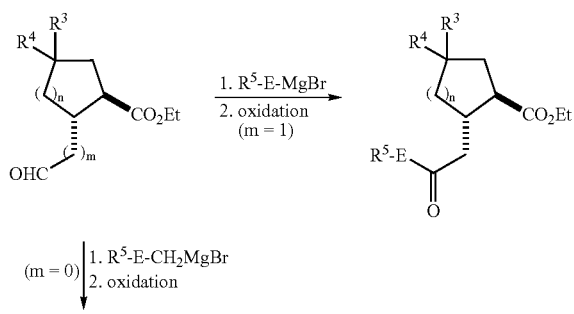

-continued

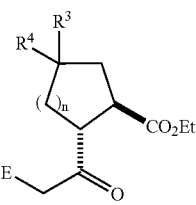

Compounds of the current invention may also be prepared according to Scheme 6. Cyclohept-4-en-1-one (Louis, J.; Bielawski, C. W.; Grubbs, R. H. *J. Am. Chem. Soc.* 2001, 123, 11312-11313) can be converted into a variety of gem-disubstituted derivatives according to the discussion accompanying Scheme 2 and further to the terminally differentiated aldehyde-ester by Schreiber ozonolysis (Schreiber, S. L.; Claus, R. E.; Reagen, J. *Tetrahedron Lett.* 1982, 23, 3867-3870). Sequential Horner-Wadsworth-Emmons type olefination, with an appropriate α phosphonylketone, and intramolecular 1,4-addition leads to an α methylene ketone that can be transformed into compounds of the current invention according to Scheme 4.

SCHEME 6

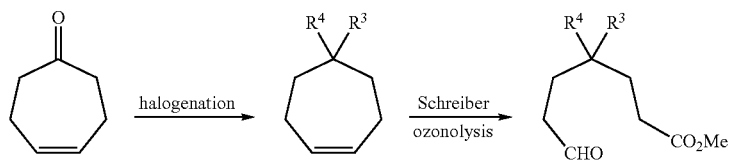

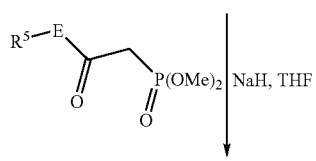

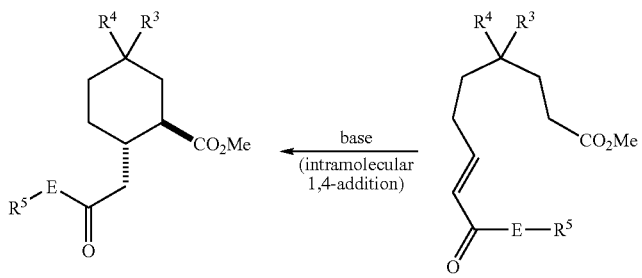

Compounds of the current invention may also be prepared according to Scheme 7. Wittig reaction of a variety of aldehydes with ethoxy(ethoxycarbonyl)methyl) triphenyiphosponium chloride yields α ketoacid derivatives after hydrolysis of the enol-ether and ester functionalities (see Bach, K. K.; El-Seedi, H. R.; Jensen, H. M.; Nielsen, H. B.; Thomsen, I.; Torssell, K. B. G. *Tetrahedron* 1994, 50, 7543-7556). A Robinson-annelation/reduction sequence (see Ziegler, F. E.; Condon, M. E. *J. Org. Chem.* 1971, 36, 3707-3713) then affords a cyclohexanone intermediate that can be transformed into compounds of the current invention according to Scheme 2.

a methylketone-derived enol-silyl ether, oxidation of the aldehyde to an acid and esterification with diazomethane yields a keto-ester that can be converted into compounds of the current invention according to Scheme 4. It will be appreciated by those skilled in the art of organic synthesis that the α,β-unsaturated aldehyde intermediate (boxed) in Scheme 8 can also be converted to compounds of the current invention according to the conjugate addition strategies detailed in Schemes 3 through 5a-c; this facet is illustrated in Scheme 9 (note analogy to Scheme 5b).

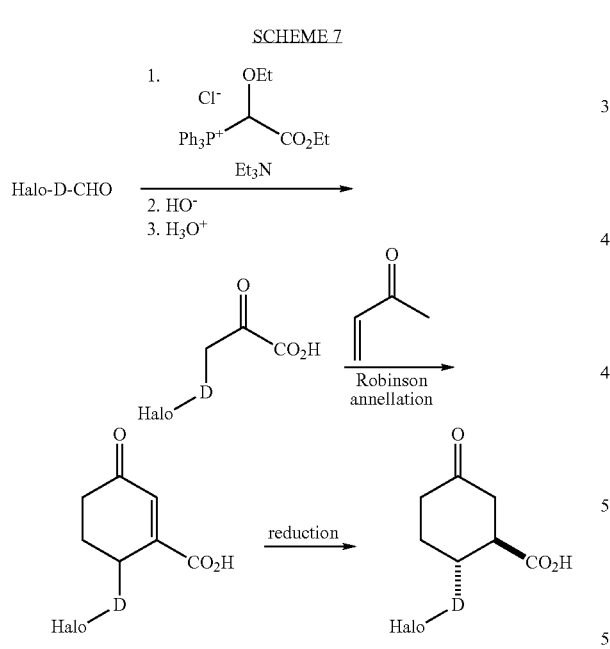

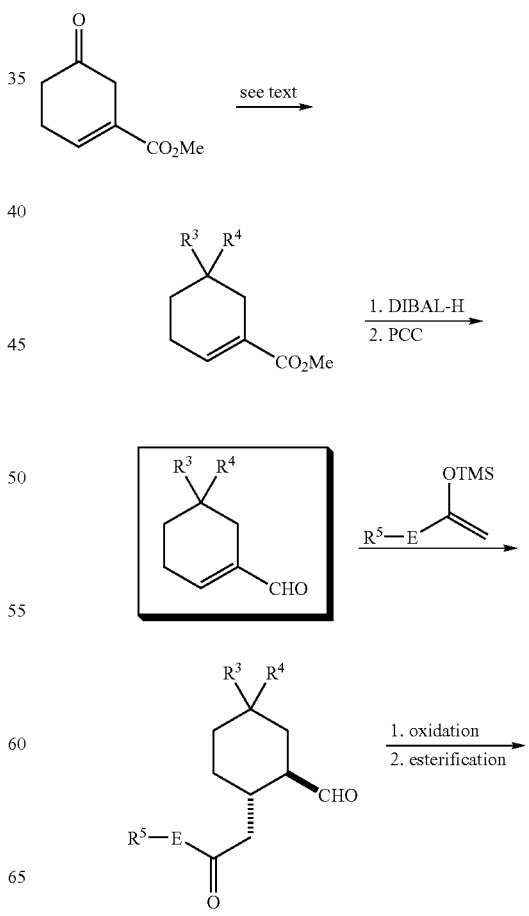

Compounds of the current invention may also be prepared according to Scheme 8. Thus, treatment of the known α,β unsaturated ketoester (see Webster, F. X.; Silverstein, R. M. *Synthesis* 1987, 922-924) with DAST or alternatively with $PCl_5$ affords the corresponding gem-diflururo ($R^3$, $R^4$=F) and gem-dichloro ($R^3$, $R^4$=F) compounds respectively. A reduction/oxidation sequence affords the α,β-unsaturated aldehyde from the ester. Iminium ion catalyzed Mukaiyama-Michael addition (see Brown, S. P.; Goodwin, N. C.; Macmillan D. W. C. *J. Am. Chem. Soc.* 2003, 125, 1192-94) of

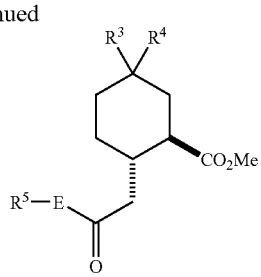

SCHEME 9

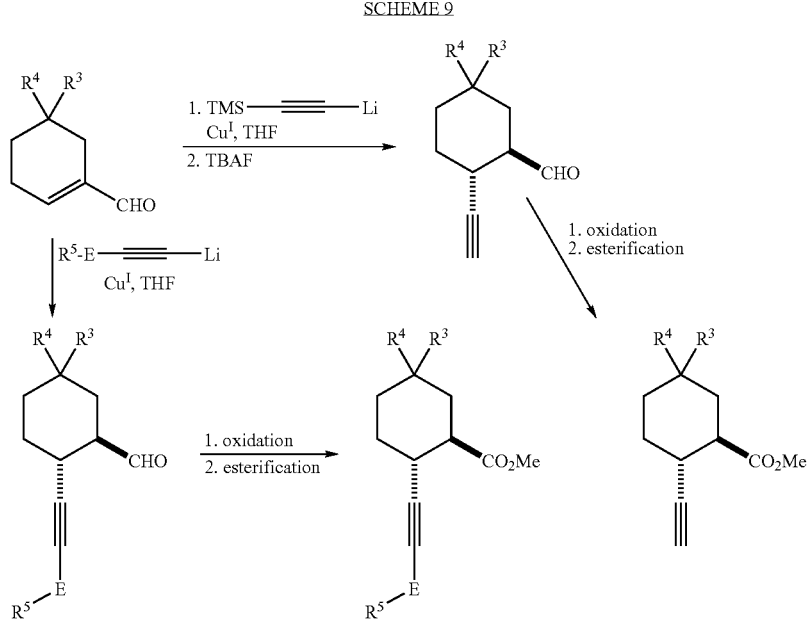

The following examples describe the synthesis of selected compounds of the current invention:

EXAMPLE 1

Synthesis of (1R,2R)-N-(Cyanomethyl)-5,5-Difluoro-2-[4'-Methylthio)-1,1'-Biphenyl-2-yl]Cyclohexanecarboxamide

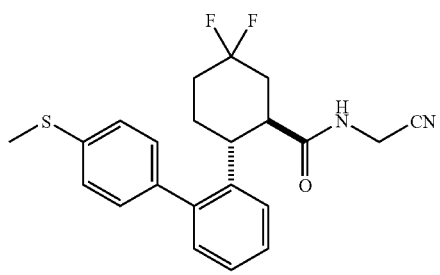

Bromotrimethylsilane (1.96 mL, 15.1 mmol) was added dropwise to a 0° C. solution of dimethyl sulfoxide (1.10 mL, 15.5 mmol) in chloroform (15 mL) with stirring at this temperature for 30 minutes. (−)-(1R,6R)-6-(2-bromophenyl)cyclohex-3-ene-1-carboxylic acid (4.24 g, 15.1 mmol; prepared in 93% ee, $[\alpha]_D$=62° (c=1.0, CHCl$_3$), by resolution of the racemic Diels-Alder adduct between 1,3-butadiene and 2-bromocinnamic acid [see Morn, R.; Manuel, C.; Mazmanian, C. *Eur. J. Med. Chem.* 1976, 11, 493-499]with (R)-phenethyl amine) was added as a solid with stirring at rt for 1 h prior to the addition of diisopropylethylamine (2.65 mL, 15.2 mmol) at 0° C. followed by reflux for 24 hours. The reaction vessel contents were then cooled to rt, diluted with ethyl acetate and washed in succession with water, 5% HCl, water and brine, and the organic phase was dried over sodium sulfate. Concentration in vacuo afforded (1R,2R,4R,5S)-4-bromo-2-(2-bromophenyl)-6-oxabicyclo[3.2.1]octan-7-one as an oily solid.

Freshly prepared sodium methoxide (0.45 M in methanol) was added to a methanol (20 mL) solution of (1R,2R,4R,5S)-4-bromo-2-(2-bromophenyl)-6-oxabicyclo [3.2.1] octan-7-one (5.43 g, 15.1 mmol) with stirrng at rt for 1.5 hours. The mixture was then treated with 0.5 M HCl (50 ml) and the methanol was removed by rotary evaporation under reduced pressure. The residue was partitioned between water and ethyl acetate and the layers separated. The aqueous phase was extracted with additional ethyl acetate and the combined organics were washed with water, 5% Na$_2$CO$_3$ (2×75 mL) and brine, and dried (Na$_2$SO$_4$). Concentration in vacuo yielded methyl (1R,2R,4R,5S)-4-bromo-2-(2-bromophenyl)-5-hydroxycyclohexanecarboxylate as a faint-yellow solid after trituration with ether/hexanes.

Freshly prepared Jones reagent (2.7 M, 7.0 mL) was added at 0° C. to an acetone (25 mL) solution of (1R,2R,4R,5S)-4-bromo-2-(2-bromophenyl)-5-hydroxycyclohexanecarboxylate (2.50 g, 6.38 mmol) with stirring at room temperature for 40 minutes. The mixture was then diluted with water and extracted with ether (3×). The combined extracts were washed with water, saturated aqueous sodium bicarbonate and brine solutions, and dried (Na$_2$SO$_4$). Concentration in vacuo gave methyl (1R,2R,4R)-4-bromo-2-(2-bromophenyl)-5-oxocyclohexanecarboxylate as a colorless, thick syrup.

A 1 M solution of KH$_2$PO$_4$ (32 mrL) was added to a slurry of methyl (1R,2R,4R)-4-bromo-2-2-bromophenyl)-5-xocyclohexanecarboxylate (2.49 g, 6.38 mmol) and zinc dust (21 g, 330 mmol) in THF (58 mL) with rapid stirring at room temperature for 1 hour. The mixture was then filtered (Celite) and the pad washed well with ethyl acetate and water. The filtrate was transferred to a separatory funnel, shaken and the layers separated. The organic phase was washed with brine and dried (Na$_2$SO$_4$). Concentration in vacuo provided methyl (1R,2R)-2-(2-bromophenyl)-5-oxocyclohexanecarboxylate as a colorless solid.

A stirred solution of methyl (1R,2R)-2-(2-bromophenyl)-5-oxocyclohexanecarboxylate (1.69 g, 5.46 mmol) in CH$_2$Cl$_2$ (23 mL) was treated at −20° C. with methanol (22 μL, 10 mol %) and diethylaminosulfur trifluoride (DAST) (1.73 mL, 13.1 mmol) with slow warming to room temperature over 1.5 hours and additional stirring at room temperature for 30 minutes. Excess reagent was quenched by the careful addition of saturated sodium bicarbonate solution at 0° C. The reaction vessel contents were then diluted with dichloromethane and washed with saturated sodium bicarbonate aqueous solution and water, and dried (Na$_2$SO$_4$). Concentration in vacuo gave methyl (1R,2R)-2-(2-bromophenyl)-5,5-difluorocyclohexanecarboxylate as a thick, brown syrup.

A 2 M aqueous solution of lithium hydroxide (26 mL) was added to a solution of methyl (1R,2R)-2-2-bromophenyl)-5,5-difluorocyclohexanecarboxylate (1.81 g, 5.46 mmol) in a mixture of methanol (20 mL) and THF (10 mL) with rapid stirring at room temperature for 15 hours. The reaction mixture was then diluted with water and extracted with ether prior to acidification to pH 2 with 2 M HCl followed by extraction with ethyl acetate (2×). The combined ethyl acetate extracts were washed with brine, dried (Na$_2$SO$_4$), and concentrated to afford (1R,2R)-2-2-bromophenyl)-5,5-difluorocyclohexanecarboxylic acid as a tan foam.

A mixture of (1R,2R)-2-(2-bromophenyl)-5,5-difluorocyclohexanecarboxylic acid (820 mg, 2.58 mmol), benzotriazol-1-yl-oxytripyrrolidinophosphonium hexafluorophosphate (1.49 g, 2.86 mmol) and aminoacetonitrile hydrochloride (530 mg, 5.73 mmol) in N,N-dimethylformamide (5.0 mL) was cooled to 0° C. and treated with triethylamine (1.26 mL, 9.04 mmol). The resulting slurry was stirred at room temperature for 2.5 hours and then poured into water and extracted with ethyl acetate (3×). The combined extracts were washed with brine and dried (Na$_2$SO$_4$). Concentration in vacuo and chromatography of the residue on silica eluting with 2/3 EtOAc/hexanes yielded (1R,2R)-2-(2-bromophenyl)-N-(cyanomethyl)-5,5-difluorocyclohexanecarboxamide as a faint-yellow foam.

(1R,2R)-2-(2-Bromophenyl)-N-(cyanomethyl)-5,5-difluorocyclohexarecarboxamide (579 mg, 1.62 mmol), 4-(methylthio) benzeneboronic acid (342 mg, 2.04 mmol), PdCl$_2$(dppf).CH$_2$Cl$_2$ (68 mg, 0.083 mmol) and 2.0 M Na$_2$CO$_3$ aqueous solution (1.22 mL, 2.44 mmol) were heated at 85° C. in N,N-dimethylformamide (4.6 mL) under a nitrogen atmosphere. After 17 hours at this temperature, the reaction mixture was cooled to room temperature and partitioned between ethyl acetate and water and the layers separated. The aqueous phase was extracted with additional ethyl acetate and the combined organics were washed with brine, and dried (Na$_2$SO$_4$). Concentration in vacuo and chromatography of the residue on silica eluting with 35/65 EtOAc/hexanes gave the title compound as a faint-yellow foam, [α]$_D$=−10° (c=1.2, CHCl$_3$), MS (−ESI): 399.2 [M−H]$^-$.

EXAMPLE 2

Synthesis Of (1R,2R)-N-(1-Cyanocyclopropyl)-5,5-Difluoro-2-[4'-(Methylthio)-1,1'-Biphenyl-2-yl]Cyclohexanecarboxamide

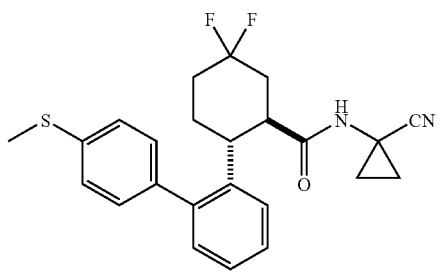

A mixture of (1R,2R)-2-(2-bromophenyt)-5,5-difluorocyclohexanecarboxylic acid, from example 1, (820 mg, 2.58 mmol), benzotriazo-1-yl-oxytripyrrolidinophosphonium hexafluorophosphate (1.48 g, 2.85 mmol) and 1-aminocyclopropanecarbonitrile hydrochloride (674 mg, 5.68 mmol) in N,N-dimethylformamide (5.0 mL) was cooled to 0° C. and treated with triethylamine (1.26 mL, 9.04 mmol). The resulting slurry was stirred at room temperature for 2.5 hours and then poured into water and extracted with ethyl acetate (3×). The combined extracts were washed with brine and dried (Na$_2$SO$_4$). Concentration in vacuo and chromatography of the residue on silica eluting with 38/62 EtOAc/hexanes yielded (1R,2R)-2-(2-bromophenyl)-N-(1-cyanocyclopropyl)-5,5-difluorocyclohexanec arboxanide as a faint-yellow solid.

(1R,2R)-2-(2-Bromophenyl)-N-(1-cyanocyclopropyl)-5,5-difluorocyclohexanecarboxamide (518 mg, 1.35 mmol), 4-(methylthio) benzeneboronic acid (285 mg, 1.70 mmol), PdCl$_2$(dppf).CH$_2$Cl$_2$ (61 mg, 0.075 mmol) and 2.0 M Na$_2$CO$_3$ aqueous solution (1.02 mL, 2.04 mmol) were heated at 85° C. in N,N-dimethylformamide (4.0 mL) under a nitrogen atmosphere. After 17 hours at this temperature, the reaction mixture was cooled to room temperature and partitioned between ethyl acetate and water and the layers separated. The aqueous phase was extracted with additional ethyl acetate and the combined organics were washed with brine, and dried (Na$_2$SO$_4$). Concentration in vacuo and chromatography of the residue on silica eluting with 30/70 EtOAc/hexanes gave the title compound as a faint-yellow foam, [α$_D$=−41° (c=0.95, CHCl$_3$), MS (−ESI): 425.3 [M−H]$^-$.

EXAMPLE 3

Synthesis of (1R/S,2R/S)-N-Cyanomethyl-5,5-Dichloro-2-[4'-(Methylthio)-1,1'-Biphenyl-2-yl]Cyclohexanecarboxamide

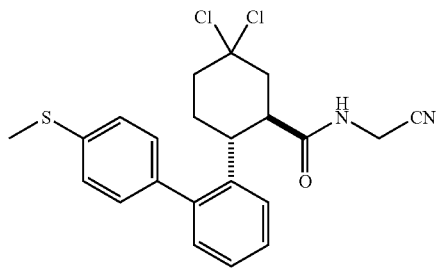

A stirred solution of methyl (1R/S,2R/S2-(2-bromophenyl)-5-oxocyclohexanecarboxylate, from example 1, (663 mg, 2.13 mmol) in toluene (1.5 mL) was treated with PCl$_5$ (1.1 g, 5.3 mmol) with stirring at room temperature for 4 hours. A 2 M solution of sodium hydroxide was then carefully added while cooling at 0° C. The mixture was partitioned between water and ether, and the layers were separated. The aqueous phase was extracted with additional ether and the combined extracts were washed with water and brine, and dried over MgSO$_4$. Concentration in vacuo and chromatography of the residue on silica gel eluting with 5/95 EtOAc/hexanes provided methyl (1R/S,2R/S)-2-(2-bromophenyl)-5,5-dichlorocyclohexanecarboxylate as a colorless solid.

The title compound was prepared as a colorless solid, MS (+ESI): 433.1 [M+H]$^+$, from methyl (1R/S,2R/S)-2-(2-bromophenyl)-5,5-dichlorocyclohexanecarboxylate according to the protocol used for the preparation of (1R,2R)-N-(cyanomethyl)-5,5-difluoro-2-[4'-(methylthio)-1,1'-biphenyl-2-yl]cyclohexanecarboxamide from methyl (1R,2R)-2-(2-bromophenyl)-5,5-difluorocyclohexanecarboxylate (see example 1).

EXAMPLE 4

Synthesis of N-(Cyanomethyl)-5,5-Difluoro-2-{1-Methyl-3-[4-(Methylthio)Phenyl]-1h-Pyrazol-4-yl}Cyclohexanecarboxamide

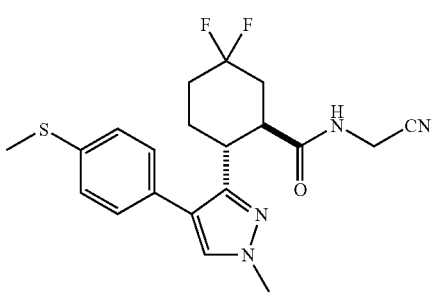

A solution of 4-bromo-1-methyl-1H-pyrazole-3-carbaldehyde (1.00 g, 5.29 mmol), malonic acid (825 mg, 7.94 mmol) and piperidine (0.12 mL, 1.2 mmol) in pyridine (0.60 mL) was heated to reflux for 3 hours. The mixture was then poured into 10% HCl and extracted with ethyl acetate (3x). The combined extracts were dried (Na$_2$SO$_4$) and concentrated in vacuo to afford (2E)-3-(4-bromo-1-methyl-1H-pyrazol-3-yl)prop-2-enoic acid as a colorless solid.

The title compound was prepared as a colorless foam, MS (+ESI): 405.2 [M+H]$^+$, from (2E)-3-(4-bromo-1-methyl-1H-pyrazol-3-yl)prop-2-enoic, acid according to the protocol used for the preparation of (1R,2R)-N-(cyanomethyl)-5,5-fluoro-2-[4'-(methylthio)-1,1'-biphenyl-2-yl]cyclohexanecarboxamide from (−)-(1R,6R)-6-(2-bromophenyl)cyclohex-3-ene-1-carboxylic acid and 1,3-butadiene (see example 1). cl EXAMPLES 5-31

The following compounds were prepared using methods analogous to those described in examples:

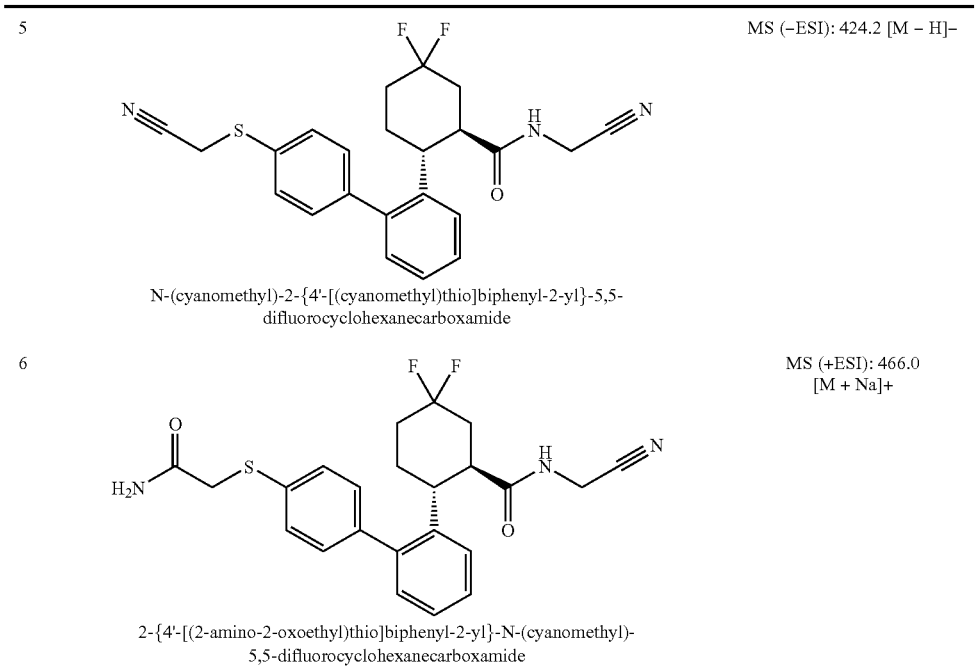

5  N-(cyanomethyl)-2-{4'-[(cyanomethyl)thio]biphenyl-2-yl}-5,5-difluorocyclohexanecarboxamide  MS (−ESI): 424.2 [M − H]−

6  2-{4'-[(2-amino-2-oxoethyl)thio]biphenyl-2-yl}-N-(cyanomethyl)-5,5-difluorocyclohexanecarboxamide  MS (+ESI): 466.0 [M + Na]+

-continued

| | | |
|---|---|---|
| 7 | 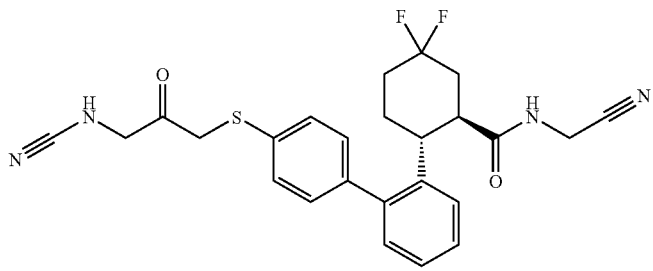

N-(cyanomethyl)-2-[4'-({2-[(cyanomethyl)amino]-2-oxoethyl}thio)biphenyl-2-yl]-5,5-difluorocyclohexanecarboxamide | MS (−ESI): 481.1 [M − H]− |
| 8 | 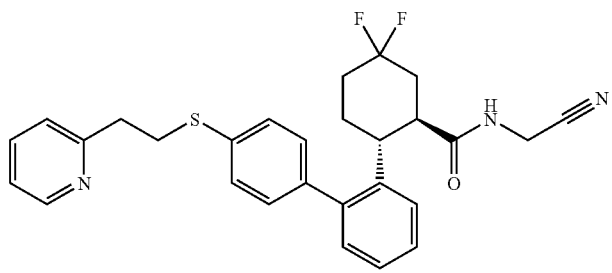

N-(cyanomethyl)-5,5-difluoro-2-{4'-[(2-pyridin-2-ylethyl)thio]biphenyl-2-yl}cyclohexanecarboxamide | MS (+ESI): 490.3 [M + H]+ |
| 9 | 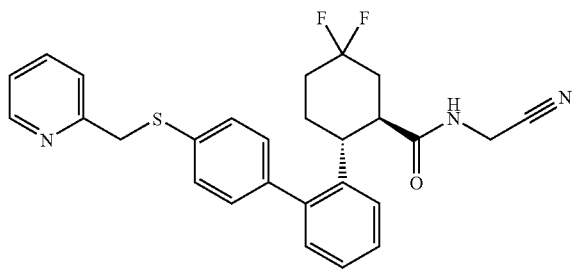

N-(cyanomethyl)-5,5-difluoro-2-{4'-[(pyridin-2-ylmethyl)thio]biphenyl-2-yl}cyclohexanecarboxamide | MS (+ESI): 500.0 [M + Na]+ |
| 10 | 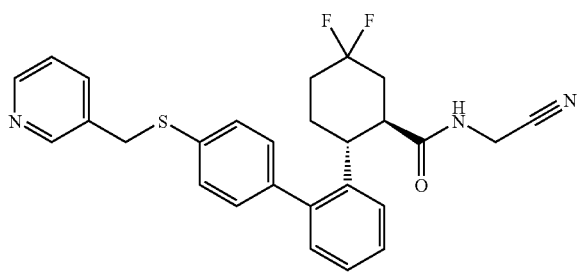

N-(cyanomethyl)-5,5-difluoro-2-{4'-[(pyridin-3-ylmethyl)thio]biphenyl-2-yl}cyclohexanecarboxamide | MS (+ESI): 500.0 [M + Na]+ |
| 11 | 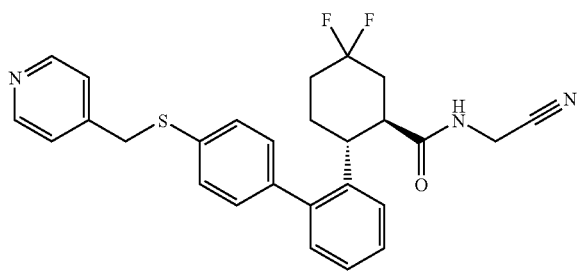

N-(cyanomethyl)-5,5-difluoro-2-{4'-[(pyridin-4-ylmethyl)thio]biphenyl-2-yl}cyclohexanecarboxamide | MS (+ESI): 500.0 [M + Na]+ |

-continued

| | | |
|---|---|---|
| 11 | 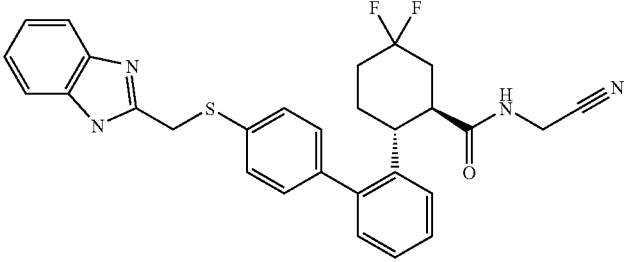<br>2-{4'-[(1H-benzimidazol-2-ylmethyl)thio]biphenyl-2-yl}-N-(cyanomethyl)-5,5-difluorocyclohexanecarboxamide | MS (+ESI): 517.1 [M + H]+ |
| 12 | 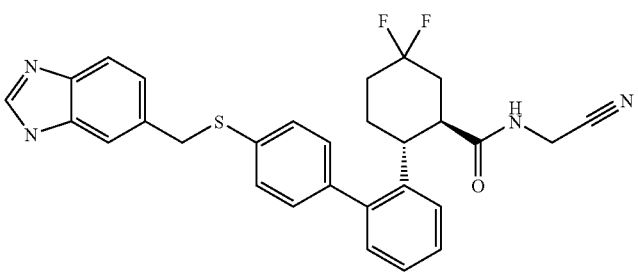<br>2-{4'-[(1H-benzimidazol-6-ylmethyl)thio]biphenyl-2-yl}-N-(cyanomethyl-5,5-difluorocyclohexanecarboxamide | MS (+ESI): 517.3 [M + H]+ |
| 13 | 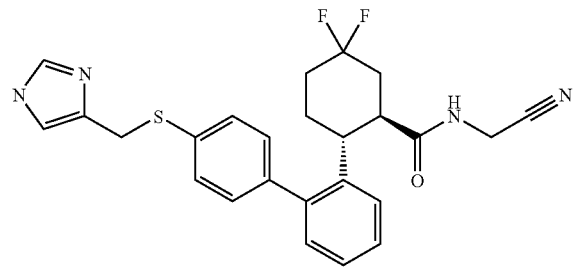<br>N-(cyanomethyl)-5,5-difluoro-2-{4'-[(1H-imidazol-4-ylmethyl)thio]biphenyl-2-yl}cyclohexanecarboxamide | MS (+ESI): 467.1 [M + H]+ |
| 14 | 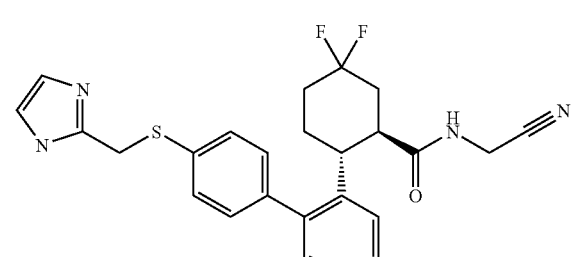<br>N-(cyanomethyl)-5,5-difluoro-2-{4'-[(1H-imidazol-2-ylmethyl)thio]biphenyl-2-yl}cyclohexanecarboxamide | MS (+ESI): 467.3 [M + H]+ |
| 15 | 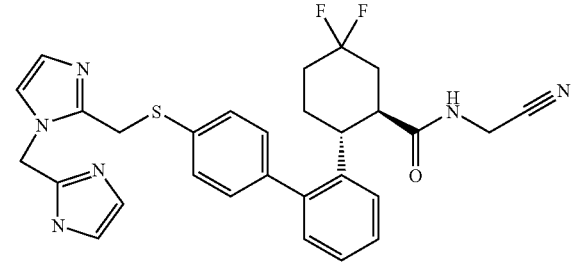<br>N-(cyanomethyl)-5,5-difluoro-2-[4'-({[1-(1H-imidazol-2-ylmethyl)-1H-imidazol-2-yl]methyl}thio)biphenyl-2-yl]cyclohexanecarboxamide | MS (+ESI): 547.3 [M + H]+ |

-continued

| | | |
|---|---|---|
| 16 | 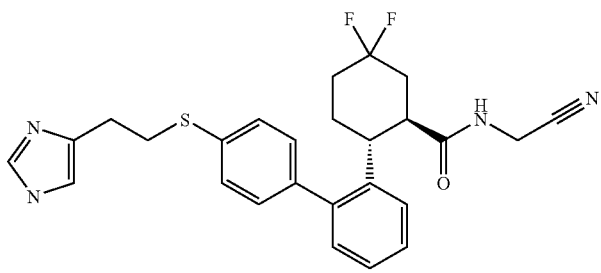<br>N-(cyanomethyl)-5,5-difluoro-2-(4'-{[2-(1H-imidazol-4-yl)ethyl]thio}biphenyl-2-yl)cyclohexanecarboxamide | MS (+ESI): 481.2 [M + H]+ |
| 17 | 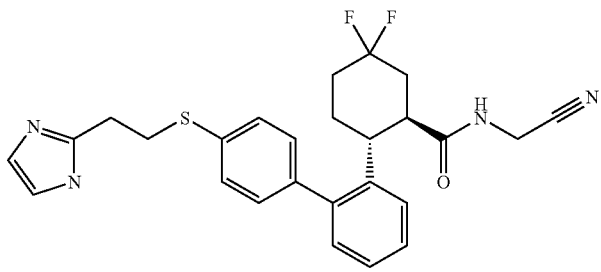<br>N-(cyanomethyl)-5,5-difluoro-2-(4'-{[2-(1H-imidazol-2-yl)ethyl]thio}biphenyl-2-yl)cyclohexanecarboxamide | MS (+ESI): 481.2 [M + H]+ |
| 18 | 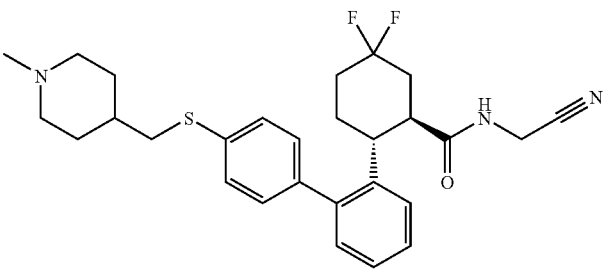<br>N-(cyanomethyl)-5,5-difluoro-2-(4'-{[(1-methylpiperidin-4-yl)methyl]thio}biphenyl-2-yl)cyclohexanecarboxamide | MS (+ESI): 498.3 [M + H]+ |
| 19 | 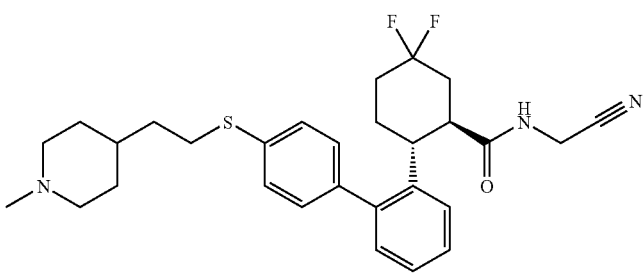<br>N-(cyanomethyl)-5,5-difluoro-2-(4'-{[2-(1-methylpiperidin-4-yl)ethyl]thio}biphenyl-2-yl)cyclohexanecarboxamide | MS (+ESI): 512.3 [M + H]+ |
| 20 | 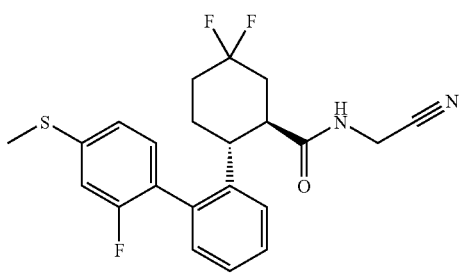<br>N-(cyanomethyl)-5,5-difluoro-2-[2'-fluoro-4'-(methylthio)biphenyl-2-yl]cyclohexanecarboxamide | MS (−APCI): 417.1 [M − H]− |

-continued

| | | |
|---|---|---|
| 21 | 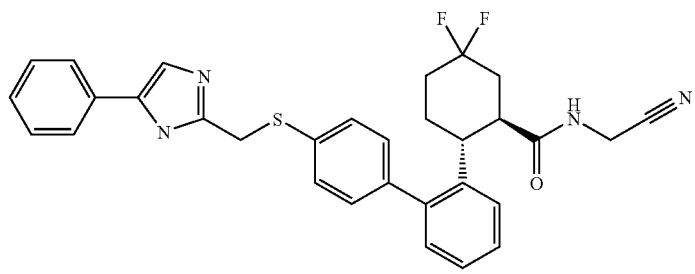 N-(cyanomethyl)-5,5-difluoro-2-(4'-{[(5-phenyl-1H-imidazol-2-yl)methyl]thio}biphenyl-2-yl)cyclohexanecarboxamide | MS (+ESI): 543.0 [M + H]+ |
| 22 | 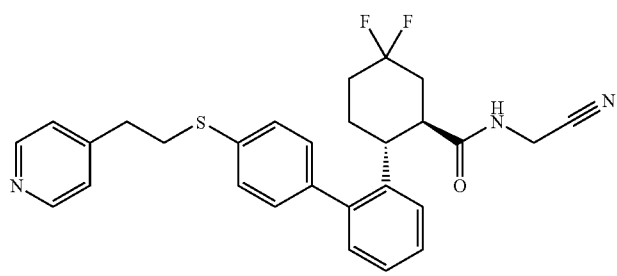 N-(cyanomethyl)-5,5-difluoro-2-{4'-[(2-pyridin-4-ylethyl)thio]biphenyl-2-yl}cyclohexanecarboxamide | MS (+ESI): 491.8 [M + H]+ |
| 23 | 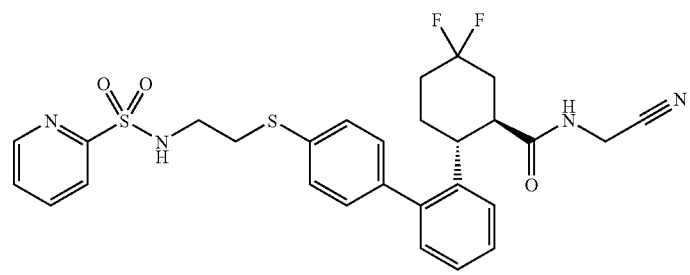 N-(cyanomethyl)-5,5-difluoro-2-[4'-({2-[(pyridin-2-ylsulfonyl)amino]ethyl}thio)biphenyl-2-yl]cyclohexanecarboxamide | MS (+ESI): 571.0 [M + H]+ |
| 24 | 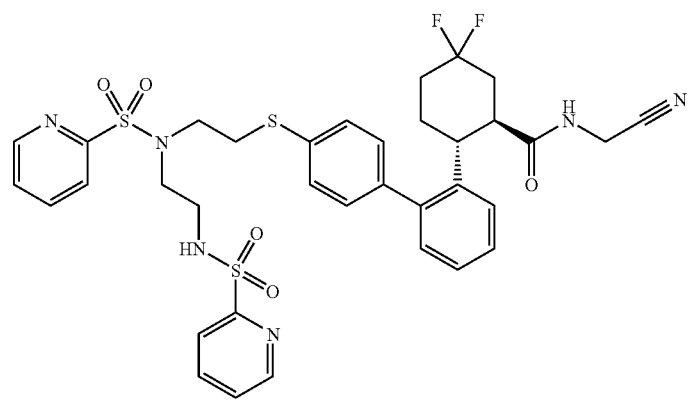 N-(cyanomethyl)-5,5-difluoro-2-(4'-{[2-((pyridin-2-ylsulfonyl){2-[(pyridin-2-ylsulfonyl)amino]ethyl}amino)ethyl]thio}biphenyl-2-yl)cyclohexanecarboxamide | MS (+ESI): 755.0 [M + H]+ |

| | | |
|---|---|---|
| 25 | 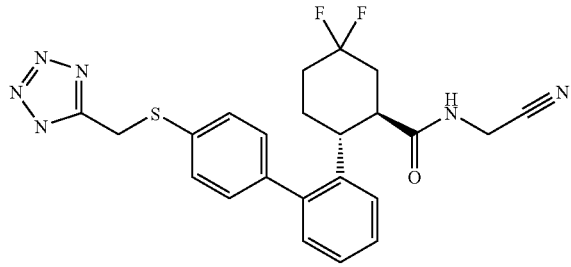<br>N-(cyanomethyl)-5,5-difluoro-2-{4'-[(1H-tetrazol-5-ylmethyl)thio]biphenyl-2-yl}cyclohexanecarboxamide | MS (−ESI): 466.8 [M − H]− |
| 26 | 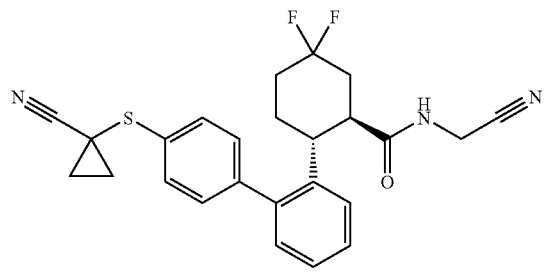<br>2-{4'-[(1-cyanocyclopropyl)thio]biphenyl-2-yl}-N-(cyanomethyl)-5,5-difluorocyclohexanecarboxamide | MS (−ESI): 450.2 [M − H]− |
| 27 | 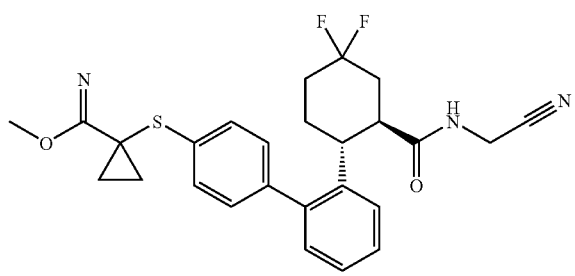<br>methyl 1-{[2'-(2-{[(cyanomethyl)amino]carbonyl}-4,4-difluorocyclohexyl)biphenyl-4-yl]thio}cyclopropanecarboximidoate | MS (+ESI): 484.2 [M + H]+ |
| 28 | 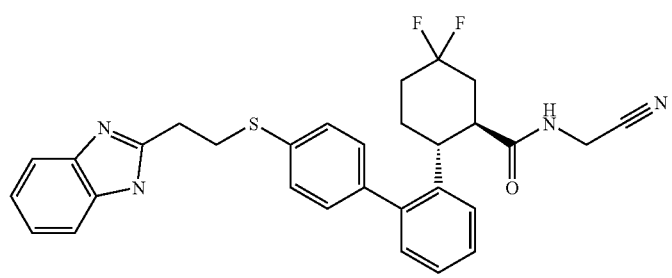<br>2-(4'-{[2-(1H-benzimidazol-2-yl)ethyl]thio}biphenyl-2-yl)-N-(cyanomethyl)-5,5-difluorocyclohexanecarboxamide | MS (+ESI): 531.2 [M + H]+ |
| 29 | 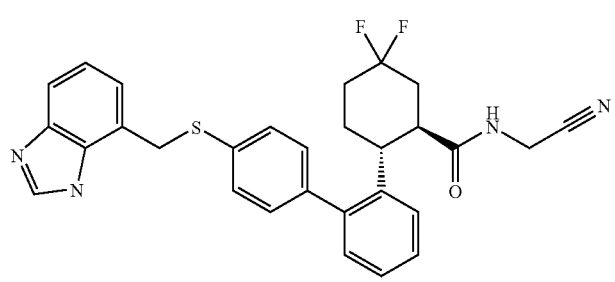<br>2-{4'-[(1H-benzimidazol-7-ylmethyl)thio]biphenyl-2-yl}-N-(cyanomethyl)-5,5-difluorocyclohexanecarboxamide | MS (+ESI): 517.1 [M + H]+ |

-continued

30

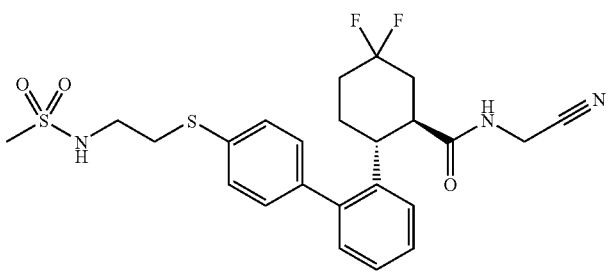

N-(cyanomethyl)-5,5-difluoro-2-[4'-({2-[(methylsulfonyl)amino]ethyl}thio)biphenyl-2-yl]cyclohexanecarboxamide

MS (−ESI): 506.2 [M − H]−

31

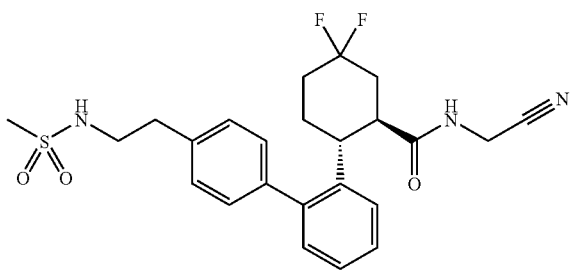

N-(cyanomethyl)-5,5-difluoro-2-(4'-{2-[(methylsulfonyl)amino]ethyl}biphenyl-2-yl)cyclohexanecarboxamide MS (+ESI): 498.1 [M + Na]+

Pharmaceutical Composition

As a specific embodiment of this invention, 100 mg of (1R,2R)-N-(cyanomethyl)-5,5-difluoro-2-[4'-(methylthio)-1,1'-biphenyl-2-yl ]cyclohexanecarboxamide, is formulated with sufficient finely divided lactose to provide a total amount of 580 to 590 mg to fill a size 0, hard-gelatin capsule.

The compounds disclosed in the present application exhibited activity in the following assays. In addition, the compounds disclosed in the present application have an enhanced pharmacological profile relative to previously disclosed compounds.

Cathepsin K Assay

Serial dilutions (1/3) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin K (0.4 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin L Assay

Serial dilutions (1/3) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin L (0.5 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathenpsin B Assay

Serial dilutions (1/3) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin B (4.0 nM) in assay buffer solution. The assay solutions were mixed for 5-10 seconds on a shaker plate and incubated for 15 minutes at room temperature. Z-Leu-Arg-AMC (8 gM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

Cathepsin S Assay

Serial dilutions (1/3) from 500 µM down to 0.0085 µM of test compounds were prepared in dimethyl sulfoxide (DMSO). Then 2 µL of DMSO from each dilution were added to 50 µL of assay buffer (MES, 50 mM (pH 5.5); EDTA, 2.5 mM; DTT, 2.5 mM and 10% DMSO) and 25 µL of human cathepsin S (20 nM) in assay buffer solution. The assay solutions were mixed for 5-10 seconds on a shaker plate and incubated for 15 minutes at room temperature. Z-Leu-Arg-AMC (8 µM) in 25 µL of assay buffer was added to the assay solutions. Hydrolysis of the coumarin leaving group (AMC) was followed by spectrofluorometry (Exλ=355 nm; Emλ=460 nm) for 10 minutes. Percent of inhibition were calculated by fitting experimental values to standard mathematical model for dose response curve.

What is claimed is:
1. A compound of the following formula:

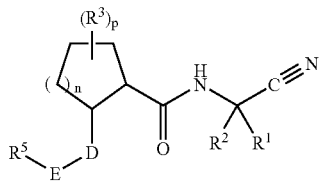

wherein
$R^1$ is hydrogen, $C_{1-6}$ alkyl or $C_{2-6}$ alkenyl wherein said alkyl and alkenyl groups are optionally substituted with $C_{3-6}$ cycloalkyl, —$SR^6$, —$SR^7$, —$SOR^6$, —$SOR^7$, —$SO_2R^6$, —$SO_2R^7$, —$SO_2CH(R^7)(R^9)$, —$OR^7$, —$OR^6$, —$N(R^7)_2$, one to six halo, aryl, heteroaryl or heterocycyl wherein said aryl, heteroaryl and heterocycyl groups are optionally substituted with one or two substitutents independently selected from the group consisting of $C_{1-6}$ alkyl, halo, hydroxyalkyl, hydroxy, alkoxy and keto;

$R^2$ is hydrogen, $C_{1-6}$ alkyl or $C_{2-6}$ alkenyl wherein said alkyl and alkenyl groups are optionally substituted with $C_{3-6}$ cycloalkyl, —$SR^6$, —$SR^7$, —$SOR^6$, —$SOR^7$, —$SO_2R^6$, —$SO_2R^7$, —$SO_2CH(R^7)(R^9)$, —$OR^7$, —$OR^6$, —$N(R^7)_2$, one to six halo, aryl, heteroaryl or heterocycyl wherein said aryl, heteroaryl and heterocycyl groups are optionally substituted with one or two substitutents independently selected from the group consisting of $C_{1-6}$ alkyl, halo, hydroxyalkyl, hydroxy, alkoxy or keto; or $R^1$ and $R^2$ can be taken together with the carbon atom to which they are attached to form a $C_{3-8}$ cycloalkyl or heterocycyl ring wherein said ring system is optionally substituted with one or two substituents independently selected from the group consisting of $C_{1-6}$ alkyl, hydroxyalkyl, haloalkyl and halo;

each $R^3$ is independently selected from the group consisting of hydrogen, halo and $C_{1-2}$ alkyl wherein said alkyl group is optionally substituted with halo; or two $R^3$ groups can be taken together with the carbon atom to which they are attached to form a $C_{3-4}$ cycloalkyl ring, wherein said group is optionally substituted with halo;

D is aryl or heteroaryl, wherein each said aryl or heteroaryl groups, which may be monocyclic or bicyclic, is optionally substituted on either the carbon or the heteroatom with one to five substituents independently selected from the group consisting of $C_{1-6}$ alkyl, haloalkyl, halo, keto, alkoxy, —$SR^6$, —$SR^7$, —$OR^6$, —$OR^7$, $N(R^7)_2$, —$SO^2R^6$ and —$SO_2R^8$;

E is aryl, wherein said aryl groups, which may be monocyclic or bicyclic, is optionally substituted on either the carbon or the heteroatom with one to five substituents independently selected from the group consisting of $C_{1-6}$ alkyl, haloalkyl, halo, keto, alkoxy, —$SR^6$, —$SR^7$, —$OR^6$, —$OR^7$, $N(R^7)_2$, —$SO_2R^6$ and —$SO_2R^8$;

$R^5$ is hydrogen, $C_{1-6}$ alkyl, $C_{2-6}$ alkenyl, $C_{2-6}$ alkynyl, $C_{1-6}$ alkyloxy, halo, nitro, cyano, aryl, heteroaryl, $C_{3-8}$ cycloalkyl, heterocyclyl, —$C(O)OR^8$, —$C(O)OSi[CH(CH_3)_2]_3$, —$OR^6$, —$OR^8$, —$C(O)R^8$, —$R^8C(O)R^6$, —$C(O)R^6$, —$C(O)N(R^a)(R^b)$, —$C(O)N(R^7)(R^7)$, —$C(O)N(R^8)(R^9)$, —$C(R^8)(R^9)OH$, —$SO_mR^7$, —$SO_mR^6$, —$R^8SR^6$, —$R^6$, —$C(R^6)_3$, —$C(R^8)(R^9)N(R^6)_2$, —$NR^8C(O)NR^8S(O)_2R^6$, —$SO_mN(R^c)(R^d)$, —$SO_mCH(R^8)(R^9)$, —$SO_m(C_{1-6}alkyl)C(O)(C_{0-6}alkyl)NR^{10}$, —$SO_m(C_{1-6}alkyl)N(R^{10})_2$, —$SO_m(C_{1-6}alkyl)R^{10}$; —$SO_m(C_{3-8}cycloalkyl)R^{10}$; —$SO_2N(R^8)C(O)(R^7)$, —$SO_2(R^8)C(O)N(R^7)_2$, —$OSO_2R^8$, —$N(R^8)(R^9)$, —$N(R^8)C(O)N(R^8)(R^6)$, —$N(R^8)C(O)R^6$, —$N(R^8)C(O)R^8$, —$N(R^8)C(O)OR^8$, —$N(R^8)SO_2(R^8)$, —$C(R^8)(R^9)NR^8C(R^8)(R^9)R^6$, —$C(R8)(R9)N(R8)R^6$, —$C(R^8)(R^9)N(R^8)(R^9)$, —$C(R^8)(R^9)SC(R^8)(R^9)(R^6)$, $R^8S$—, —$C(R^a)(R^b)Nr^aC(R^a)(R^b)(R^6)$, —$C(R^a)(R^b)N(R^a)(R^b)$, —$C(R^a)(R^b)C(R^a)(R^b)N(R^a)(R^b)$, —$C(O)C(R^a)(R^b)N(R^a)(R^b)$, —$C(R^a)(R^b)N(R^a)C(O)R^6$, —$C(O)C(R^a)(R^b)S(R^a)$, $C(R^a)(R^b)C(O)N(R^a)(R^b)$, —$B(OH)_2$, —$OCH_2O$— or 4,4,5,5-tetramethyl-1,3,2-dioxaborolan-2-yl; wherein said groups are optionally substituted on either the carbon or the heteroatom with one to five substituents independently selected from the group consisting of $C_{1-6}$ alkyl, halo, keto, cyano, haloalkyl, hydroxyalkyl, —$OR^6$, —$OR^7$, —$NO_2$, —$NH_2$, —$NHS(O)_2R^8$, —$R^6SO_2R^7$, —$SO_2R^7$, —$SO(R^7)$, —$SR^7$, —$SR^6$, —$SO_mN(R^c)(R^d)$, —$SO_mN(R^8)C(O)(R^7)$, $C(R^8)(R^9)N(R^8)(R^9)$, —$C(R^8)(R^9)OH$, —$COOH$, —$C(O)(O)(R^7)$, —$C(O)(O)C(R^7)_3$, —$C(R^a)(R^b)C(O)N(R^a)(R^b)$, —$C(O)(R^a)$, —$N(R^8)C(R^8)(R^9)(R^6)$, —$N(R^8)CO(R^6)$, —$NH(CH_2)_2OH$, —$NHC(O)OR^8$, —$Si(CH_3)_3$, heterocyclyl, aryl, heteroaryl, $(C_{1-4}alkyl)heteroaryl$ and $(C_{1-4}alkyl)aryl$;

$R^6$ is hydrogen, aryl, aryl$(C_{1-4})$alkyl, $(C_{1-4}alkyl)$aryl, heteroaryl, heteroaryl$(C_{1-4})$alkyl, $(C_{1-4}alkyl)$heteroaryl, $C_{3-8}$ cycloalkyl, $C_{3-8}$ cycloalkyl$(C_{1-4})$alkyl, or heterocyclyl$(C_{1-4})$alkyl wherein said groups can be optionally substituted with one, two, or three substituents independently selected from the group consisting of halo, alkoxy and —$SO_2R^7$;

$R^7$ is hydrogen or $C_{1-6}$ alkyl which is optionally substituted with one, two, or three substituents independently selected from the group consisting of halo, alkoxy, cyano, —$N(R^8)(R^9)$ and —$SR^8$;

$R^8$ is hydrogen or $C_{1-6}$ alkyl $R^9$ is hydrogen or $C_{1-6}$ alkyl;

$R^{10}$ is hydrogen, $C_{1-6}$ alkyl, cyano, aryl, heteroaryl, heterocyclyl, $SO_m$heteroaryl, $(C=N)O(C_{1-6}alkyl)$ or $(C_{1-6}alkyl)NH(SO_m)heteroaryl$;

$R^a$ is hydrogen, $C_{1-6}$ alkyl, $(C_{1-6}$ alkyl)aryl, $(C_{1-6}$ alkyl)hydroxyl, —$O(C_{1-6}$ alkyl), hydroxyl, halo, aryl, heteroaryl, $C_3$-8 cycloalkyl or heterocyclyl, wherein said alkyl, aryl, heteroaryl, $C_{3-8}$ cycloalkyl and heterocycyl can be optionally substituted on either the carbon or the heteroatom with one, two, or three substituents independently selected from $C_{1-6}$ alkyl or halo;

$R^b$ is hydrogen, $C_{1-6}$ alkyl, $(C_{1-6}$ alkyl)aryl, $(C_{1-6}$ alkyl)hydroxyl, alkoxyl, hydroxyl, halo, aryl, heteroaryl, $C_{3-8}$ cycloalkyl or heterocycyl, wherein said alkyl, aryl, heteroaryl, $C_{3-8}$ cycloalkyl and heterocycyl can be optionally substituted on either the carbon or the heteroatom with one, two, or three substituents independently selected from group consisting of $C_{1-6}$ alkyl and halo; or $R^a$ and $R^b$ can be taken together with the carbon atom to which they are attached or are between them to form a $C_{3-8}$ cycloalkyl ring or $C_{3-8}$ heterocycyl ring wherein said 3-8 membered ring system may be optionally substituted with one or two substituents independently selected from $C_{1-6}$ alkyl and halo;

$R^c$ is hydrogen or $C_{1-6}$ alkyl which is optionally substituted with one, two, or three substituents independently selected from the group consisting of halo and —$OR^6$;

$R^d$ is hydrogen or $C_{1-6}$ alkyl which is optionally substituted with one, two, or three substituents independently selected from the group consisting of halo and —$OR^6$; or $R^c$ and $R^d$ can be taken together with the nitrogen atom to which they are attached or are between them to form a $C_{3-8}$ heterocycyl ring which is optionally substituted with one or two substituents independently selected from the group consisting of $C_{1-6}$ alkyl, halo hydroxyalkyl, hydroxy, alkoxy and keto;

n is two;

m is an integer from zero to two;

p is an integer from one to three;

or a pharmaceutically acceptable salts or stereoisomers thereof.

2. The compound of claim 1 wherein D is aryl or heteroaryl and E is aryl or heteroaryl.

3. The compound of claim 1 wherein each $R^3$ is independently selected from hydrogen or halo.

4. The compound of claim 2 wherein $R^5$ is —$SO_mR^7$, —$SO_mR^6$, —$R^8SR^6$, $SO_mN(R^c)(R^d)$, —$SO_mCH(R^8)(R^9)$, —$SO_m(C_{1-6}alkyl)C(O)(C_{0-6}alkyl)NR^{10}$, —$SO_m(C_{1-6}alkyl)N(R^{10})_2$, —$SO_m(C_{1-6}alkyl)R^{10}$; —$SO_m(C_{3-8}cycloalkyl)R^{10}$; —$SO_2N(R^8)C(O)(R^7)$ or —$SO_2(R^8)C(O)N(R^7)_2$; wherein said groups are optionally substituted on either the carbon or the heteroatom with one to five substituents independently selected from the group consisting of $C_{1-6}$ alkyl, halo, keto, cyano, haloalkyl, hydroxyalkyl, —$OR^6$, —$OR^7$, —$NO_2$, —$NH_2$, —$NHS(O)_2R^8$, —$R^6SO_2R^7$, —$SO_2R^{7,}$ —$SO(R7)$, —$SR^7$, —$SR^6$, —$SO_mN(R^c)(R^d)$, —$SO_mN(R^8)C(O)(R^7)$, —$C(R^8)(R^9)N(R^8)(R^9)$, —$C(R^8)(R^9)OH$, —COOH, —$C(O)(O)(R^7)$, —$C(O)(O)C(R^7)_3$, —$C(R^a)(R^b)C(O)N(R^a)(R^b)$, —$C(O)(R^a)$, —$N(R^8)C(R^8)(R^9)(R^6)$, —$N(R^8)CO(R^6)$, —$NH(CH_2)_2OH$, —$NHC(O)OR^8$, —$Si(CH_3)_3$, heterocyclyl, aryl, heteroaryl, $(C_{1-4}alkyl)$heteroaryl and $(C_{1-4}alkyl)$aryl.

5. The compound of claim 4 wherein $R^1$ is hydrogen, $R^2$ is hydrogen, or $R^1$ and $R^2$ can be taken together with the carbon atom to which they are attached to form a $C_{3-8}$ cycloalkyl ring wherein said ring system is optionally substituted with one or two substituents independently selected from $C_{1-6}$ alkyl, hydroxyalkyl, haloalkyl, or halo.

6. The compound of claim 1 selected from:

N-(cyanomethyl)-5,5-difluoro-2-[4'-(methylthio)-1,1'-biphenyl-2-yl]cyclohexanecarboxamide;

N-(1-cyanocyclopropyl)-5,5-difluoro-2-[4'-(methylthio)-1,1'-biphenyl-2-yl]cyclohexanecarboxamide;

2-[4'-(benzyloxy)-1,1'-biphenyl-2-yl]-N-(cyanomethyl)cyclohexanecarboxamide;

N-(cyanomethyl)-2-(4'-hydroxy-1,1'-biphenyl-2-yl)cyclohexanecarboxamide;

N-(cyanomethyl)-2-(4'-fluoro-1,1'-biphenyl-2-yl)cyclohexanecarboxamide;

N-(cyanomethyl)-2-[4'-(methylsulfonyl)-1,1'-biphenyl-2-yl]cyclohexanecarboxamide;

N-(cyanomethyl)-5,5-difluoro-2-(4'-fluoro-1,1'-biphenyl-2-yl)cyclohexanecarboxamide;

N-(cyanomethyl)-2-(4'-vinyl-1,1'-biphenyl-2-yl)cyclohexanecarboxamide;

N-(cyanomethyl)-2-(4'-cyclopropyl-1,1'-biphenyl-2-yl)cyclohexanecarboxamide;

N-(cyanomethyl)-5,5-difluoro-2-[5-(methylsulfonyl)-4'-(methylthio)-1,1'-biphenyl-2-yl]cyclohexanecarboxamide;

N-(1-cyanocyclopropyl)-5,5-difluoro-2-[5-(methylsulfonyl)-4'-(methylthio)-1,1'-biphenyl-2-yl]cyclohexanecarboxamide;

N-(cyanomethyl)-2-{4'-[(fluoromethyl)thio]-1,1'-biphenyl-2-yl}cyclohexanecarboxamide;

N-(cyanomethyl)-2-(2'-methyl-1,1'-biphenyl-2-yl)cyclohexanecarboxamide;

N-(cyanomethyl)-2-(4'-methyl-1,1'-biphenyl-2-yl)cyclohexanecarboxamide;

N-(cyanomethyl)-2-(4'-ethyl-1,1'-biphenyl-2-yl)cyclohexanecarboxamide;

N-(cyanomethyl)-2-(4'-propyl-1,1'-biphenyl-2-yl)cyclohexanecarboxamide;

N-(cyanomethyl)-2-(3'-isopropyl-1,1'-biphenyl-2-yl)cyclohexanecarboxamide;

N-(cyanomethyl)-2-(4'-isopropyl-1,1'-biphenyl-2-yl)cyclohexanecarboxamide;

2-(4'-tert-butyl-1,1'-biphenyl-2-yl)-N-(cyanomethyl)cyclohexanecarboxamide;

N-(cyanomethyl)-2-[3'-(trifluoromethyl)-1,1'-biphenyl-2-yl]cyclohexanecarboxamide;

N-(cyanomethyl)-2-(3'-fluoro-1,1'-biphenyl-2-yl)cyclohexanecarboxamide;

N-(cyanomethyl)-2-(2'-fluoro-1,1'-biphenyl-2-yl)cyclohexanecarboxamide;

2-(4'-chloro-1,1'-biphenyl-2-yl)-N-(cyanomethyl)cyclohexanecarboxamide;

2-(3'-chloro-1,1'-biphenyl-2-yl)-N-(cyanomethyl)cyclohexanecarboxamide;

N-(cyanomethyl)-2-[3'-(hydroxymethyl)-1,1'-biphenyl-2-yl]cyclohexanecarboxamide;

2'-(2-{[(cyanomethyl)amino]carbonyl}cyclohexyl)-1,1'-biphenyl-3-carboxylic acid;

2'-(2-{[(cyanomethyl)amino]carbonyl}cyclohexyl)-1,1'-biphenyl-4-carboxylic acid;

N-(cyanomethyl)-2-(3'-methoxy-1,1'-biphenyl-2-yl)cyclohexanecarboxamide;

N-(cyanomethyl)-2-(2'-ethoxy-1,1'-biphenyl-2-yl)cyclohexanecarboxamide;

N-(cyanomethyl)-2-(4'-ethoxy-1,1'-biphenyl-2-yl)cyclohexanecarboxamide;

N-(cyanomethyl)-2-(3'-isopropoxy-1,1-biphenyl-2-yl)cyclohexanecarboxamide;

N-(cyanomethyl)-2-(4'-isopropoxy-1,1'-biphenyl-2-yl)cyclohexanecarboxamide;

N-(cyanomethyl)-2-(4'-phenoxy-1,1'-biphenyl-2-yl)cyclohexanecarboxamide;

N-(cyanomethyl)-2-[4'-(trifluoromethoxy)-1,1'-biphenyl-2-yl]cyclohexanecarboxamide;

N-(cyanomethyl)-2-[2'-(methylthio)-1,1'-biphenyl-2-yl]cyclohexanecarboxamide;

N-(cyanomethyl)-2-[3'-(methylthio)-1,1'-biphenyl-2-yl]cyclohexanecarboxamide;

N-(cyanomethyl)-2-[4'-(ethylthio)-1,1'-biphenyl-2-yl]cyclohexanecarboxamide;

2-(3'-amino-1,1'-biphenyl-2-yl)-N-(cyanomethyl)cyclohexanecarboxamide;

N-(cyanomethyl)-2-[4'-(dimethylamino)-1,1'-biphenyl-2-yl]cyclohexanecarboxamide;

N-(cyanomethyl)-2-(3'-nitro-1,1'-biphenyl-2-yl)cyclohexanecarboxamide;

2-[3'-(acetylamino)-1,1'-biphenyl-2-yl]-N-(cyanomethyl)cyclohexanecarboxamide;

N-(cyanomethyl)-2-(4'-isobutyl-1,1'-biphenyl-2-yl)cyclohexanecarboxamide;
N-(cyanomethyl)-2-(2-pyridin-4-ylphenyl)cyclohexanecarboxamide;
N-(cyanomethyl)-2-(2-quinolin-8-ylphenyl)cyclohexanecarboxamide;
N-(cyanomethyl)-2-[2-(2-methoxypyrimidin-5-yl)phenyl]cyclohexanecarboxamide;
N-(cyanomethyl)-2-(2-pyridin-3-ylphenyl)cyclohexanecarboxamide;
N-(cyanomethyl)-2-(2-thien-3-ylphenyl)cyclohexanecarboxamide;
2-(4'-acetyl-1,1'-biphenyl-2-yl)-N-(cyanomethyl)cyclohexanecarboxamide;
N-(cyanomethyl)-2-(1,1':2',1''-terphenyl-2-yl)cyclohexanecarboxamide;
2-(4'-cyano-1,1'-biphenyl-2-yl)-N-(cyanomethyl)cyclohexanecarboxamide;
2-(3'-cyano-1,1'-biphenyl-2-yl)-N-(cyanomethyl)cyclohexanecarboxamide;
tert-butyl 4-[3'-(2-{[(cyanomethyl)amino]carbonyl}cyclohexyl)-1,1'-biphenyl-4-yl]piperazine-1-carboxylate;
N-(cyanomethyl)-2-(4'-piperazin-1-yl-1,1'-biphenyl-3-yl)cyclohexanecarboxamide;
N-(cyanomethyl)-2-(4'-methoxy-1,1'-biphenyl-3-yl)cyclohexanecarboxamide;
N-(cyanomethyl)-2-[4'-(methylthio)-1,1'-biphenyl-3-yl]cyclohexanecarboxamide;
N-(cyanomethyl)-2-[4'-(methylsulfonyl)-1,1'-biphenyl-3-yl]cyclohexanecarboxamide;
N-(cyanomethyl)-2-(5-phenyl-1,3-oxazol-2-yl)cyclohexanecarboxamide;
N-(cyanomethyl)-2-(5-phenyl-1,3-thiazol-2-yl)cyclohexanecarboxamide;
N-(cyanomethyl)-2-(5-phenyl-1,3-thiazol-2-yl)cyclohexanecarboxamide;
N-(cyanomethyl)-2-[4'-(methylthio)-1,1'-biphenyl-2-yl]cyclohexanecarboxamide;
N-(cyanomethyl)-5,5-dichloro-2-[4'-(methylthio)-1,1'-biphenyl-2-yl]cyclohexanecarboxamide;
N-(cyanomethyl)-5,5-difluoro-2-{1-methyl-3-[4-(methylthio)phenyl]-1H-pyrazol-4-yl}cyclohexanecarboxamide;
N-(cyanomethyl)-6-[4'-(methylthio)-1,1'-biphenyl-2-yl]spiro[2.5]octane-5-carboxamide;
N-(cyanomethyl)-2-{4'-[(cyanomethyl)thio]biphenyl-2-yl}-5,5-difluorocyclohexanecarboxamide;
2-{4'-[(2-amino-2-oxoethyl)thio]biphenyl-2-yl}-N-(cyanomethyl)-5,5-difluorocyclohexanecarboxamide;
N-(cyanomethyl)-2-[4'-({2-[(cyanomethyl)amino]-2-oxoethyl}thio)biphenyl-2-yl]-5,5-difluorocyclohexanecarboxamide;
N-(cyanomethyl)-5,5-difluoro-2-{4'-[(2-pyridin-2-ylethyl)thio]biphenyl-2-yl}cyclohexanecarboxamide;
N-(cyanomethyl)-5,5-difluoro-2-{4'-[(pyridin-2-ylmethyl)thio]biphenyl-2-yl}cyclohexanecarboxamide;
N-(cyanomethyl)-5,5-difluoro-2-{4'-[(pyridin-3-ylmethyl)thio]biphenyl-2-yl}cyclohexanecarboxamide;
N-(cyanomethyl)-5,5-difluoro-2-{4'-[(pyridin-4-ylmethyl)thio]biphenyl-2-yl}cyclohexanecarboxamide;
2-{4'-[(1H-benzimidazol-2-ylmethyl)thio]biphenyl-2-yl}-N-(cyanomethyl)-5,5-difluorocyclohexanecarboxamide;
2-{4'-[(1H-benzimidazol-6-ylmethyl)thio]biphenyl-2-yl}-N-(cyanomethyl)-5,5-difluorocyclohexanecarboxamide;
N-(cyanomethyl)-5,5-difluoro-2-{4'-[(1H-imidazol-4-ylmethyl)thio]biphenyl-2-yl}cyclohexanecarboxamide;
N-(cyanomethyl)-5,5-difluoro-2-{4'-[(1H-imidazol-2-ylmethyl)thio]biphenyl-2-yl}cyclohexanecarboxamide;
N-(cyanomethyl)-5,5-difluoro-2-[4'-({[1-(1H-imidazol-2-ylmethyl)-1H-imidazol-2-yl]methyl}thio)biphenyl-2-yl]cyclohexanecarboxamide;
N-(cyanomethyl)-5,5-difluoro-2-(4'-{[2-(1H-imidazol-4-yl)ethyl]thio}biphenyl-2-yl)cyclohexanecarboxamide;
N-(cyanomethyl)-5,5-difluoro-2-(4'-{[2-(1H-imidazol-2-yl)ethyl]thio}biphenyl-2-yl)cyclohexanecarboxamide;
N-(cyanomethyl)-5,5-difluoro-2-(4'-{[(1-methylpiperidin-4-yl)methyl]thio}biphenyl-2-yl)cyclohexanecarboxamide;
N-(cyanomethyl)-5,5-difluoro-2-(4'-{[2-(1-methylpiperidin-4-yl)ethyl]thio}biphenyl-2-yl)cyclohexanecarboxamide;
N-(cyanomethyl)-5,5-difluoro-2-[2'-fluoro-4'-(methylthio)biphenyl-2-yl]cyclohexanecarboxamide;
N-(cyanomethyl)-5,5-difluoro-2-(4'-{[(5-phenyl-1H-imidazol-2-yl)methyl]thio}biphenyl-2-yl)cyclohexanecarboxamide;
N-(cyanomethyl)-5,5-difluoro-2-{4'-[(2-pyridin-4-ylethyl)thio]biphenyl-2-yl}cyclohexanecarboxamide;
N-(cyanomethyl)-5,5-difluoro-2-[4'-({2-[(pyridin-2-ylsulfonyl)amino]ethyl}thio)biphenyl-2-yl]cyclohexanecarboxamide;
N-(cyanomethyl)-5,5-difluoro-2-(4'-{[2-((pyridin-2-ylsulfonyl){2-[(pyridin-2-ylsulfonyl)amino]ethyl}amino)ethyl]thio}biphenyl-2-yl)cyclohexanecarboxamide;
N-(cyanomethyl)-5,5-difluoro-2-{4'-[(1H-tetrazol-5-ylmethyl)thio]biphenyl-2-yl}cyclohexanecarboxamide;
2-{4'-[(1-cyanocyclopropyl)thio]biphenyl-2-yl}-N-(cyanomethyl)-5,5-difluorocyclohexanecarboxamide;
methyl 1-{[2'-(2-{[(cyanomethyl)amino]carbonyl}-4,4-difluorocyclohexyl)biphenyl-4-yl]thio}cyclopropanecarboximidoate;
2-(4'-{[2-(1H-benzimidazol-2-yl)ethyl]thio}biphenyl-2-yl)-N-(cyanomethyl)-5,5-difluorocyclohexanecarboxamide;
2-{4'-[(1H-benzimidazol-7-ylmethyl)thio]biphenyl-2-yl}-N-(cyanomethyl)-5,5-difluorocyclohexanecarboxamide;
N-(cyanomethyl)-5,5-difluoro-2-[4'-({2-[(methylsulfonyl)amino]ethyl}thio)biphenyl-2-yl]cyclohexanecarboxamide and
N-(cyanomethyl)-5,5-difluoro-2-(4'-{2-[(methylsulfonyl)amino]ethyl}biphenyl-2-yl)cyclohexanecarboxamide;
or a pharmaceutically acceptable salt or stereoisomer thereof.

7. A pharmaceutical composition comprising a compound according to claim 1 and a pharmaceutically acceptable carrier.

* * * * *